US009573992B2

(12) United States Patent
Dombrecht et al.

(10) Patent No.: US 9,573,992 B2
(45) Date of Patent: *Feb. 21, 2017

(54) SERUM ALBUMIN BINDING PROTEINS

(75) Inventors: Bruno Dombrecht, Heusden (BE);
Peter Schotte, De Pinte (BE); Cedric Jozef Neotere Ververken, Merelbeke (BE)

(73) Assignee: Ablynx N.V., Zwijnaarde (BE)

( * ) Notice: Subject to any disclaimer, the term of this patent is extended or adjusted under 35 U.S.C. 154(b) by 332 days.

This patent is subject to a terminal disclaimer.

(21) Appl. No.: 14/128,719

(22) PCT Filed: Jun. 14, 2012

(86) PCT No.: PCT/EP2012/061304
§ 371 (c)(1),
(2), (4) Date: Mar. 19, 2014

(87) PCT Pub. No.: WO2012/175400
PCT Pub. Date: Dec. 27, 2012

(65) Prior Publication Data
US 2014/0228546 A1 Aug. 14, 2014

Related U.S. Application Data

(60) Provisional application No. 61/500,464, filed on Jun. 23, 2011.

(51) Int. Cl.
C07K 16/18 (2006.01)
C07K 16/28 (2006.01)
C07K 16/32 (2006.01)

(52) U.S. Cl.
CPC ........... *C07K 16/18* (2013.01); *C07K 16/2863* (2013.01); *C07K 16/32* (2013.01); *C07K 2317/22* (2013.01); *C07K 2317/31* (2013.01); *C07K 2317/565* (2013.01); *C07K 2317/567* (2013.01); *C07K 2317/569* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,608,039 A | 3/1997 | Pastan et al. | |
| 7,741,273 B2 | 6/2010 | McKay | |
| 7,867,497 B2 | 1/2011 | Crowe, Jr. | |
| 8,337,845 B2 | 12/2012 | Park et al. | |
| 8,460,888 B2 | 6/2013 | Lafaye et al. | |
| 8,703,135 B2 * | 4/2014 | Beste ................ | C07K 16/2863 424/133.1 |
| 8,940,298 B2 | 1/2015 | Wu et al. | |
| 2008/0057063 A1 | 3/2008 | Rinkenberger et al. | |
| 2012/0244164 A1 | 9/2012 | Beste et al. | |
| 2014/0199295 A1 | 7/2014 | Baumeister et al. | |
| 2014/0205597 A1 | 7/2014 | Baumeister et al. | |
| 2014/0294847 A1 | 10/2014 | Beste et al. | |
| 2014/0341903 A1 | 11/2014 | Beste et al. | |
| 2015/0344568 A1 | 12/2015 | Baumeister et al. | |
| 2016/0009816 A1 | 1/2016 | Ritter et al. | |

FOREIGN PATENT DOCUMENTS

| | | | | |
|---|---|---|---|---|
| BE | WO 2012042026 A1 * | 4/2012 | ......... | C07K 16/2863 |
| JP | 2008-539772 | 11/2008 | | |
| JP | 2010-505435 | 2/2010 | | |
| JP | 2010-518062 | 5/2010 | | |
| NL | WO 2006122787 A1 * | 11/2006 | ............ | C07K 16/18 |
| RU | 2357974 C2 | 6/2009 | | |
| RU | 2007142444 A | 6/2009 | | |
| WO | WO 2004/041862 A2 | 5/2004 | | |
| WO | WO 2004/041865 A2 | 5/2004 | | |
| WO | WO 2004/044204 A2 | 5/2004 | | |
| WO | WO 2004/062551 A2 | 7/2004 | | |
| WO | WO 2006/015371 A2 | 2/2006 | | |
| WO | WO 2006/122786 A2 | 11/2006 | | |
| WO | WO 2006/129828 A2 | 12/2006 | | |
| WO | WO 2006/129843 A2 | 12/2006 | | |
| WO | WO 2007/085814 A1 | 8/2007 | | |
| WO | WO 2007/126799 A2 | 11/2007 | | |
| WO | WO 2008/020079 A1 | 2/2008 | | |
| WO | WO 2008/028977 A2 | 3/2008 | | |
| WO | WO 2008/043821 A1 | 4/2008 | | |
| WO | WO 2008/096158 A2 | 8/2008 | | |
| WO | WO 2008/122787 A1 | 10/2008 | | |

(Continued)

OTHER PUBLICATIONS

Rudikoff et al., Proc Natl Acad Sci U S A. Mar. 1982;79(6):1979-83.*
Janeway et al., Immunobiology, 3rd edition, 19097, Garland Press, pp. 3:1-3:11.*
Ghahroudi et al., FEBS Lett. Sep. 15, 1997;414(3):521-6.*
[No Author Listed] Ablynx presentation. Sep. 9, 2015. P11-008-PCT-1.
European Medicines Agency, Guideline on immunogenicity assessment of monoclonal antibodies intended for in vivo clinical use. Nov. 18, 2010.
Birchmeier et al., Met, metastasis, motility and more. Nat Rev Mol Cell Biol. Dec. 2003;4(12):915-25.
Bottaro et al., Identification of the hepatocyte growth factor receptor as the c-met proto-oncogene product. Science. Feb. 15, 1991;251(4995):802-4.
Burgess et al., Fully human monoclonal antibodies to hepatocyte growth factor with therapeutic potential against hepatocyte growth factor/c-Met-dependent human tumors. Cancer Res. Feb. 1, 2006;66(3):1721-9. Erratum in: Cancer Res. Jun. 1, 2006;66(11):5976.
Cao et al., Neutralizing monoclonal antibodies to hepatocyte growth factor/scatter factor (HGF/SF) display antitumor activity in animal models. Proc Natl Acad Sci U S A. Jun. 19, 2001;98(13):7443-8.
Cooper et al., Molecular cloning of a new transforming gene from a chemically transformed human cell line. Nature. Sep. 6-11, 1984;311(5981):29-33.

(Continued)

*Primary Examiner* — Michael Szperka
(74) *Attorney, Agent, or Firm* — Wolf, Greenfield & Sacks, P.C.

(57) ABSTRACT

The present invention relates to amino acid sequences that are capable of binding to serum albumin; to proteins and polypeptides comprising or essentially consisting of such amino acid sequences; to nucleic acids that encode such amino acid sequences, proteins or polypeptides; to compositions, and in particular pharmaceutical compositions, that comprise such amino acid sequences, proteins and polypeptides; and to uses of such amino acid sequences, proteins and polypeptides.

20 Claims, 17 Drawing Sheets

(56) References Cited

FOREIGN PATENT DOCUMENTS

| WO | WO 2008/142164 A2 | 11/2008 |
|---|---|---|
| WO | WO 2009/007427 A2 | 1/2009 |
| WO | WO 2009/068627 A2 | 6/2009 |
| WO | WO 2009/068628 A1 | 6/2009 |
| WO | WO 2009/138519 A1 | 11/2009 |
| WO | WO 2009/147248 A2 | 12/2009 |
| WO | WO 2010/042815 A2 | 4/2010 |
| WO | WO 2010/108937 A2 | 9/2010 |
| WO | WO 2011/064382 A1 | 6/2011 |
| WO | WO 2011/073954 A2 | 6/2011 |
| WO | WO 2011/110642 A2 | 9/2011 |
| WO | WO 2013/024059 A2 | 2/2013 |

OTHER PUBLICATIONS

Deffar et al., Nanobodies—the new concept in antibody engineering. African Journal of Biotechnology. 2009;8(12):2645-2652.
Gibbs, Nanobodies. Sci Am. Aug. 2005;293(2):78-83.
Holliger et al., Engineered antibody fragments and the rise of single domains. Nat Biotechnol. Sep. 2005;23(9):1126-36.
Kakkar et al., Pharmacokinetics and safety of a fully human hepatocyte growth factor antibody, AMG 102, in cynomolgus monkeys. Pharm Res. Oct. 2007;24(10):1910-8. Epub May 23, 2007.
Klimov, Spontaneous emission of an atom in the presence of nanobodies. Quantum Electronics. 2001;31(7):569-586.
Liu et al, Targeting the c-MET signaling pathway for cancer therapy. Expert Opin Investig Drugs. Jul. 2008;17(7):997-1011.
Loyet et al., Technology comparisons for anti-therapeutic antibody and neutralizing antibody assays in the context of an anti-TNF pharmacokinetic study. J Immunol Methods. Jun. 30, 2009;345(1-2):17-28. doi: 10.1016/j.jim.2009.03.012. Epub Apr. 2, 2009.
Matsumoto et al., NK4 (HGF-antagonist/angiogenesis inhibitor) in cancer biology and therapeutics. Cancer Sci. Apr. 2003;94(4):321-7.
Mire-Sluis et al., Recommendations for the design and optimization of immunoassays used in the detection of host antibodies against biotechnology products. J Immunol Methods. Jun. 2004;289(1-2):1-16.
Muyldermans et al., Recognition of antigens by single-domain antibody fragments: the superfluous luxury of paired domains. Trends Biochem Sci. Apr. 2001;26(4):230-5.
Nguyen et al., Improved gene transfer selectivity to hepatocarcinoma cells by retrovirus vector displaying single-chain variable fragment antibody against c-Met. Cancer Gene Ther. Nov. 2003;10(11):840-9.
Nieba et al., Disrupting the hydrophobic patches at the antibody variable/constant domain interface: improved in vivo folding and physical characterization of an engineered scFv fragment. Protein Eng. Apr. 1997;10(4):435-44.
Peng et al., Clinical immunogenicity specificity assessments: a platform evaluation. J Pharm. Biomed Anal. Feb. 20, 2011;54(3):629-35. doi: 10.1016/j.jpba.2010.09.035. Epub Oct. 29, 2010.
Poelmans et al., Immunogenicity monitoring during preclinical development of Nanobodies: comparing assay formats and species matrices. The AAPS Journal. vol. 12. No. S1. Jan. 1, 2010.
Ponzetto et al., A novel recognition motif for phosphatidylinositol 3-kinase binding mediates its association with the hepatocyte growth factor/scatter factor receptor. Mol Cell Biol. Aug. 1993;13(8):4600-8.
Revets et al., Nanobodies as novel agents for cancer therapy. Expert Opin Biol Ther. Jan. 2005;5(1):111-24.
Routledge et al., Reshaping antibodies for therapy—5. Prospects for producing non-immunogenic monoclonal antibodies. 1996. last accessed at http://www.path.cam.ac.uk/~mrc7/reshaping/index.html on Apr. 23, 2014.

Shankar et al., Recommendations for the validation of immunoassays used for detection of host antibodies against biotechnology products. J Pharm Biomed Anal. Dec. 15, 2008;48(5):1267-81. doi:10.1016/j.jpba.2008.09.020. Epub Sep. 19, 2008.
Skottrup et al., Diagnostic evaluation of a nanobody with picomolar affinity toward the protease RgpB from Porphyromonas gingivalis. Anal Biochem. Aug. 15, 2011;415(2):158-67. doi: 10.1016/j.ab.2011.04.015. Epub Apr. 20, 2011.
Strothmeyer et al., Comparative analysis of predicted HLA binding of immunoglobulin idiotype sequences indicates T cell mediated immunosurveillance in follicular lymphoma. Blood. Sep. 9, 2010;116(10):1734-6. doi: 10.1182/blood-2010-02-270199. Epub Jun. 3, 2010.
Subramanyam, Immunogenicity considerations for biologics. FABIAN. Presentation on Nov. 6, 2008.
Trojan et al., Immunoglobulin framework-derived peptides function as cytotoxic T-cell epitopes commonly expressed in B-cell malignancies. Nat Med. Jun. 2000;6(6):667-72.
PCT/EP2011/067132, Dec. 22, 2011, International Search Report.
PCT/EP2011/067132, Apr. 11, 2013, International Preliminary Report on Patentability.
PCT/EP2012/061304, Sep. 5, 2012, International Search Report and Written Opinion.
PCT/EP2012/061304, Sep. 19, 2013, International Preliminary Report on Patentability.
PCT/EP2012/062251, Dec. 18, 2012, International Search Report and Written Opinion.
PCT/EP2012/062251, Oct. 15, 2013, International Preliminary Report on Patentability.
PCT/EP2012/069373, Jan. 14, 2013, Invitation to Pay Additional Fees.
PCT/EP2012/069373, Apr. 29, 2013, International Search Report and Written Opinion.
Conrath et al., Camel single-domain antibodies as modular building units in bispecific and bivalent antibody constructs. J Biol Chem. Mar. 9, 2001;276(10):7346-50. Epub Oct. 25, 2000.
Cortez-Retamozo et al., Efficient tumor targeting by single-domain antibody fragments of camels. Int J Cancer. Mar. 20, 2002;98(3):456-62.
Davies et al., 'Camelising' human antibody fragments: NMR studies on VH domains. FEBS Lett. Feb. 21, 1994;339(3):285-90.
Davies et al., Single antibody domains as small recognition units: design and in vitro antigen selection of camelized, human VH domains with improved protein stability. Protein Eng. Jun. 1996;9(6):531-7.
Gottlin et al., Isolation of novel EGFR-specific VHH domains. J Biomol Screen. Jan. 2009;14(1):77-85. doi: 10.1177/1087057108327064.
Keyaerts et al., Phase I Study of 68Ga-HER2-Nanobody for PET/CT Assessment of HER2 Expression in Breast Carcinoma. J Nucl Med. Jan. 2016;57(1):27-33.doi:10.2967/jnumed.115.162024. Epub Oct. 8, 2015.
Lin, Pharmacokinetics of biotech drugs: peptides, proteins and monoclonal antibodies. Curr Drug Metab. Sep. 2009;10(7):661-91.
Roitt et al., Immunology. Moscow, Mir. 2000;110-111.
Roovers et al., Efficient inhibition of EGFR signaling and of tumour growth by antagonistic anti-EFGR Nanobodies. Cancer Immunol Immunother. Mar. 2007;56(3):303-317.
Tibbitts et al., Key factors influencing ADME properties of therapeutic proteins: A need for ADME characterization in drug discovery and development. MAbs. Feb.-Mar. 2016;8(2):229-45. doi:10-1080/19420862.2015.1115937. Epub Dec. 4, 2015.
Tijink et al., Improved tumor targeting of anti-epidermal growth factor receptor Nanobodies through albumin binding: taking advantage of modular Nanobody technology. Mol Cancer Ther. Aug. 2008;7(8):2288-97. doi:10-1158/1535-7163.MCT-07-2384.

* cited by examiner

Figure 2

|        | EVQLLESGGG | LVQPGGSLRL | SCAASGFTFR | SFGMSWVRQA | PGKGPEWVSS | ISGSGSDTLY | ADSVKGRFTI | SRDNSKNTLY | 80 |
|--------|------------|------------|------------|------------|------------|------------|------------|------------|----|
| Alb-23 | ........... | ........... | ........... | ........... | ........... | ........... | ........... | ........... | 80 |
| Alb-23A | A.......... | ........... | ........... | ........... | ........... | ........... | ........... | ........... | 80 |
| Alb-23B | A.......... | ........... | ........... | ........... | ........... | ........... | ........... | ........... | 80 |
| Alb-23C | ........... | ........... | ........... | ........... | ........... | ........... | ........... | ........... | 80 |
| Alb-23D | ........... | ........... | ........... | ........... | ........... | ........... | ........... | ........... | 80 |
| Alb-23E | ........... | ........... | ........... | ........... | ........... | ........... | ........... | ........... | 80 |
| Alb-23F | ........... | ........... | ........... | ........... | ........... | ........... | ........... | ........... | 80 |
| Alb-23G | ........... | ........... | ........... | ........... | ........... | ........... | ........... | ........... | 80 |
| Alb-23H | ........... | ........... | ........... | ........... | ........... | ........... | ........... | ........... | 80 |
| Alb-23I | ........... | ........... | ........... | ........... | ........... | ........... | ........... | ........... | 80 |

|        | LQMNSLRPED | TAVYYCTIGG | SLSRSSQGTL | VTVSS       |     |
|--------|------------|------------|------------|-------------|-----|
| Alb-23  | ........... | ........... | ........... | .....       | 115 |
| Alb-23A | ........... | ........... | ........... | .....       | 115 |
| Alb-23B | ........... | ........... | .......Q.. | .....       | 115 |
| Alb-23C | ........... | ........... | .......Q.. | .....       | 115 |
| Alb-23D | ........... | ........... | ........... | .....A--    | 116 |
| Alb-23E | ........... | ........... | ........... | .....AA-    | 117 |
| Alb-23F | ........... | ........... | ........... | .....AAA    | 118 |
| Alb-23G | ........... | ........... | ........... | .....G--    | 116 |
| Alb-23H | ........... | ........... | ........... | .....GG-    | 117 |
| Alb-23I | ........... | ........... | ........... | .....GGG    | 118 |

Figure 3

| Sequence name | SEQ ID | Sequence |
|---|---|---|
| Alb-23 | 1 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb-1 (WO 06/122787) | 2 | AVQLVESGGGLVQPGNSLRLSCAASGFTFRSFGMSWVRQAPGKEPEWVSSISGSGSDTLYADSVKGRFTISRDNAKTTLYLQMNSLKPEDTAVYYCTIGGSLSRSSQGTQVTVSS |
| Alb-23A | 3 | AVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb-23B | 4 | AVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTQVTVSS |
| Alb-23C | 5 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTQVTVSS |
| Alb-23D | 6 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSA |
| Alb-23E | 7 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSAA |
| Alb-23F | 8 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSAAA |
| Alb-23G | 9 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSG |

Figure 3 (continued):

| Sequence name | SEQ ID | Sequence |
|---|---|---|
| Alb-23H | 10 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSGG |
| Alb-23I | 11 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSGGG |
| 4E09 (US 61/451,869) | 12 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSS |
| 04E09 (L49S) | 13 | EVQLVESGGGLVQPGGSLRLSCAASGFILDYYAIGWFRQAPGKEREGVSCIDASDDITYYADSVKGRFTISRDNAKNTVYLQMNSLKPEDTGVYYCATPIGLSSSCLLEYDYDYWGQGTLVTVSS |
| 04E09 (C50S/C100bG) | 14 | EVQLVESGGGLVQPGGSLRLSCAASGFILDYYAIGWFRQAPGKEREGVLSIDASDDITYYADSVKGRFTISRDNAKNTVYLQMNSLKPEDTGVYYCATPIGLSSSGLLEYDYDYWGQGTLVTVSS |
| 04E09 (C22A/C92S) | 15 | EVQLVESGGGLVQPGGSLRLSAAASGFILDYYAIGWFRQAPGKEREGVLCIDASDDITYYADSVKGRFTISRDNAKNTVYLQMNSLKPEDTGVYYSATPIGLSSSCLLEYDYDYWGQGTLVTVSS |
| A00790067 = 4E09 (Q108L) | 16 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSS |

Figure 3 (continued):

| Sequence name | SEQ ID | Sequence |
|---|---|---|
| A00790068 = 4E09 (A74S, K83R, Q108L) | 17 | EVQLVESGGGLVQPGGSLRLSCAASGFILDYYAIGWFRQAPGKEREGVLCIDASDDITYYADSVKGRFTISRDNSKNTVYLQMNSLRPEDTGVYYCATPIGLSSSCLLEYDYDYWGQGTLVTVSS |
| A00790069 4E09 = (A74S, K83R, G88A, Q108L) | 18 | EVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSS |
| A00790105 4E09 = (E1D, A74S, K83R, G88A, Q108L) | 19 | DVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSS |
| Alb23-9GS-4E09 | 20 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSGGGGSGGGSEVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSS |
| 4E09-9GS-Alb23 (A007900057) | 21 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSSGGGGSGGGSEVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |

Figure 3 (continued):

| Sequence name | SEQ ID | Sequence |
|---|---|---|
| Alb23-9GS-A00790105 | 22 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSGGGGSGGGSDVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSS |
| A00790105-9GS-Alb23 (A007901219) | 23 | DVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSSGGGGSGGGSEVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| Alb23-35GS-4E09 | 24 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSGGGGSGGGGSGGGGSGGGGSGGGGSGGGGSEVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSS |
| 4E09-35GS-Alb23 (A007900058) | 25 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSSGGGGSGGGGSGGGGSGGGGSGGGGSGGGGSGGGGSEVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |

Figure 3 (continued):

| Sequence name | SEQ ID | Sequence |
|---|---|---|
| Alb23-35GS-A00790105 | 26 | EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSSGGGGSGGGGSGGGGSGGGGSGGGGSGGGGSGGGGSDVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSS |
| A00790105-35GS-Alb23 | 27 | DVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSSGGGGSGGGGSGGGGSGGGGSGGGGSGGGGSGGGGSEVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| A00790105-35GS-A00790105-35GS-Alb23 | 28 | DVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSSGGGGSGGGSDVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSSGGGGSGGGSEVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |
| CDR1 | 29 | SFGMS |
| CDR2 | 30 | SISGSGSDTLYADSVKG |
| CDR3 | 31 | GGSLSR |

Figure 3 (continued):

| Sequence name | SEQ ID | Sequence |
|---|---|---|
| ALB4 (WO 06/122787: SEQ ID NO: 58) | 32 | EVQLVESGGGLVQPGGSLRLSCAASGFTFSSFGMSWVRQAPGKEPEWVSSISGSGSDTLYADSVKGRFTISRDNAKTTLYLQMNSLKPEDTAVYYCTIGGSLSRSSQGTQVTVSS |
| ALB5 (WO 06/122787: SEQ ID NO: 59) | 33 | EVQLVESGGGLVQPGGSLRLSCAASGFTFRSFGMSWVRQAPGKGLEWVSSISGSGSDTLYADSVKGRFTISRDNAKTTLYLQMNSLKPEDTAVYYCTIGGSLSRSSQGTQVTVSS |
| ALB6 (WO 06/122787: SEQ ID NO: 60) | 34 | EVQLVESGGGLVQPGNSLRLSCAASGFTFRSFGMSWVRQAPGKGLEWVSSISGSGSDTLYADSVKGRFTISRDNAKTTLYLQMNSLKPEDTAVYYCTIGGSLSRSSQGTLVTVSS |
| ALB7 (WO 06/122787: SEQ ID NO: 61) | 35 | EVQLVESGGGLVQPGNSLRLSCAASGFTFRSFGMSWVRQAPGKGLEWVSSISGSGSDTLYADSVKGRFTISRDNAKTTLYLQMNSLRPEDTAVYYCTIGGSLSRSSQGTLVTVSS |
| ALB8 (WO 06/122787: SEQ ID NO: 62) | 36 | EVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| ALB9 (WO 06/122787: SEQ ID NO: 63) | 37 | EVQLVESGGGLVQPGNSLRLSCAASGFTFSSFGMSWVRQAPGKGLEWVSSISGSGSDTLYADSVKGRFTISRDNAKNTLYLQMNSLRPEDTAVYYCTIGGSLSRSSQGTLVTVSS |

Figure 3 (continued):

| Sequence name | SEQ ID | Sequence |
|---|---|---|
| ALB10 (WO 06/122787: SEQ ID NO: 64) | 38 | EVQLVESGGGLVQPGNSLRLSCAASGFTFSSFGMSWVRQAPGKGLEWVSSISGSGSDTLYADSVKGRFTISRDNAKNTLYLQMNSLRPEDTAVYYCTIGGSLSRSGQGTLVTVSS |
| A007900009 (4E09-9GS-ALB11-Flag3-His6) | 39 | EVQLVESGGGLVQPGGSLRLSCAASGFILDYYAIGWFRQAPGKEREGVLCIDASDDITYYADSVKGRFTISRDNAKNTVYLQMNSLKPEDTGVYYCATPIGLSSSCLLEYDYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGAADYKDHDGDYKDHDIDYKDDDDKGAAHHHHHH |
| A007900171 (A00790105 - 9GS-Alb11) | 40 | DVQLVESGGGLVQPGGSLRLSCAASGFILDYYAIGWFRQAPGKEREGVLCIDASDDITYYADSVKGRFTISRDNSKNTVYLQMNSLRPEDTAVYYCATPIGLSSSCLLEYDYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| IGE045-9GS-ALB23 | 41 | EVQLLESGGGLVQPGGSLRLSCAASGFTFGNYDMAWVRQAPGKRPEWVSSIDTGGDITHYADSVKGRFTISRDNAKNTLYLQMNSLRPEDTAVYWCATDEEYALGPNEFDYYGQGTLVTVSSGGGGSGGGSEVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |

Figure 3 (continued):

| Sequence name | SEQ ID | Sequence |
|---|---|---|
| IGE045-9GS-ALB11 | 42 | EVQLLESGGGLVQPGGSLRLSCAASGFTFGNYDMAWVRQAPGKRPEWVSSIDTGGDITHYADSVKGRFTISRDNAKNTLYLQMNSLRPEDTAVYWCATDEEYALGPNEFDYYGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| IGE0045 | 43 | EVQLLESGGGLVQPGGSLRLSCAASGFTFGNYDMAWVRQAPGKRPEWVSSIDTGGDITHYADSVKGRFTISRDNAKNTLYLQMNSLRPEDTAVYWCATDEEYALGPNEFDYYGQGTLVTVSS |
| OX40L079 (PCT/EP2010/069606, SEQ ID NO: 229) | 44 | DVQLVESGGGLVQPGGSLRLSCAASGRTFSSIYAKGWFRQAPGKEREFVAAISRSGRSTSYADSVKGRFTISRDNSKNTVYLQMNSLRPEDTAVYYCAAVGGATTVTASEWDYWGQGTLVTVSSGGGGSGGGGSGGGGSGGGGSGGGGSGGGGSEVQLVESGGGLVQPGGSLRLSCAASGRTFSSIYAKGWFRQAPGKEREFVAAISRSGRSTSYADSVKGRFTISRDNSKNTVYLQMNSLRPEDTAVYYCAAVGGATTVTASEWDYWGQGTLVTVSSGGGGSGGGGSGGGGSGGGGSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |

Figure 3 (continued):

| Sequence name | SEQ ID | Sequence |
|---|---|---|
| OX40L089 | 45 | DVQLVESGGGLVQPGGSLRLSCAASGRTFSSIYAKGWFRQA PGKEREFVAAISRSGRSTSYADSVKGRFTISRDNSKNTVYLQ MNSLRPEDTAVYYCAAVGGATTVTASEWDYWGQGTLVTV SSGGGGSGGGGSGGGGSGGGGSGGGGSGGGGSGGGGSEVQ LVESGGGLVQPGGSLRLSCAASGRTFSSIYAKGWFRQAPGK EREFVAAISRSGRSTSYADSVKGRFTISRDNSKNTVYLQMNS LRPEDTAVYYCAAVGGATTVTASEWDYWGQGTLVTVSSG GGGSGGGGSGGGGSGGGGSGGGGSGGGGSGGGGSEVQLLE SGGGLVQPGGSLRLSCAASGFTFRSFGMSWVRQAPGKGPE WVSSISGSGSDTLYADSVKGRFTISRDNSKNTLYLQMNSLRP EDTAVYYCTIGGSLSRSSQGTLVTVSS |
| A007901222 | 46 | DVQLVESGGGLVQPGGSLRLSCAASGFILDYYAIGWFRQAP GKEREGVLCIDASDDITYYADSVKGRFTISRDNSKNTVYLQ MNSLRPEDTAVYYCATPIGLSSSCLLEYDYDYWGQGTLVTV SSGGGGSGGGSEVQLLESGGGLVQPGGSLRLSCAASGFTFRS FGMSWVRQAPGKGPEWVSSISGSGSDTLYADSVKGRFTISR DNSKNTLYLQMNSLRPEDTAVYYCTIGGSLSRSSQGTLVTV SSA |
| A007901256 | 47 | DVQLVESGGGLVQPGGSLRLSCAASGFAFDDYAIGWFRQAP GEEREGVSSISSTYGLTYYADSVKGRFTISSDNSKNTVYLQM NSLRPEDTAVYYCAATPIGLIGLDAYEYDYWGQGTLVTVSS GGGGSGGGSEVQLVESGGGLVQPGNSLRLSCAASGFTFSSF GMSWVRQAPGKGLEWVSSISGSGSDTLYADSVKGRFTISRD NAKTTLYLQMNSLRPEDTAVYYCTIGGSLSRSSQGTLVTVSS A |

Figure 3 (continued):

| Sequence name | SEQ ID | Sequence |
|---|---|---|
| A007901259 | 48 | DVQLVESGGGLVQPGGSLRLSCAASGFTFDDYAIGWFRQAPGEERLGVSSISSTYGLTYYADSVKGRFTISSDNSKNTVYLQMNSLRPEDTAVYYCAATPIGLIGLDAYEYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |
| A007901260 | 49 | DVQLVESGGGLVQPGGSLRLSCAASGFAFDDYAIGWFRQAPGEERLGVSSISSTYGLTYYADSVKGRFTISSDNSKNTVYLQMNSLRPEDTAVYYCAATPIGLIGLDAYEYDYWGQGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSA |

Figure 5

| construct | A007900171 | | | | |
|---|---|---|---|---|---|
| CN | L | L | H | H | H |

SERUM ALBUMIN BINDING PROTEINS

RELATED APPLICATIONS

This application is a national stage filing under 35 U.S.C. §371 of international application PCT/EP2012/061304, filed Jun. 14, 2012, which was published under PCT Article 21(2) in English, and claims the benefit under 35 U.S.C. §119(e) of U.S. provisional application Ser. No. 61/500,464, filed Jun. 23, 2011, the disclosures of which are incorporated by reference herein in their entireties.

The present invention relates to amino acid sequences that are capable of binding to serum albumin; to proteins and polypeptides comprising or essentially consisting of such amino acid sequences; to nucleic acids that encode such amino acid sequences, proteins or polypeptides; to compositions, and in particular pharmaceutical compositions, that comprise such amino acid sequences, proteins and polypeptides; and to uses of such amino acid sequences, proteins and polypeptides.

Other aspects, embodiments, advantages and applications of the invention will become clear from the further description herein.

If any terms are not specifically defined herein, these terms have the meaning given to them in WO 2009/068627 or WO 06/122787. If any terms used herein are not specifically defined herein or in WO 2009/068627/WO 06/122787, then they have their usual meaning in the art, for which reference is for example made to the standard handbooks.

Amino acid sequences that are capable of binding to human serum albumin and uses thereof in polypeptide constructs in order to increase the half-life of therapeutically relevant proteins and polypeptides are known in the art.

For example, WO 04/041865 by applicant describes Nanobodies directed against serum albumin (and in particular against human serum albumin) that can be linked to other proteins (such as one or more other Nanobodies directed against a desired target) in order to increase the half-life of said protein.

The international application WO 06/122787 describes a number of Nanobodies against (human) serum albumin. These Nanobodies include the Nanobody called Alb-1 (SEQ ID NO: 52 in WO 06/122787) and humanized variants thereof, such as Alb-8 (SEQ ID NO: 62 in WO 06/122787). [Nanobody® and Nanobodies® are trademarks of Ablynx N.V.]. Again, these can be used to extend the half-life of therapeutic proteins and polypeptide and other therapeutic entities or moieties.

As of the date of first filing of the present application, the use of Nanobodies against (human) serum albumin for extending the half-life of therapeutic moieties such as Nanobodies has been validated by means of clinical trials. For example, the safety, tolerability, immunogenicity and pharmacokinetics (PK) of ALX-0141, a protein construct that comprises two Nanobodies against RANK-L and one Nanobody against human serum albumin, has been confirmed in phase I clinical trials (data presented by Ablynx N.V. on May 27, 2011 at the Annual European Congress of Rheumatology (EULAR) in London). Also, numerous published patent applications of Ablynx N.V. give examples of constructs with increased half-life that comprise one or more Nanobodies against a therapeutic target and one or more Nanobodies against serum albumin (such as Alb-8). Reference is for example made to WO 04/041862, WO 2006/122786, WO 2008/020079, WO 2008/142164, WO 2009/068627 and WO 2009/147248.

Although it has been established that the use of Nanobodies against (human) serum albumin (such as those described in WO 04/041865 and WO 06/122787, and in particular the humanized variants of Alb-1 described in WO 06/122787) provide a good and broadly applicable methodology for extending the half-life of Nanobodies and of other therapeutic moieties and entities, this does not mean that the skilled person would not benefit from having further improved Nanobodies against human serum albumin at his disposal for this purpose.

The present invention provides such an improved Nanobody that is directed against human serum albumin (called "Alb-23"; see SEQ ID NO:1), as well as a number of variants of this Nanobody (also referred to herein as "Alb-23 like sequences" or "Alb-23 variants", see SEQ ID NO's 3 to 11 for some non-limiting examples), as well as as compounds, polypeptides and other (protein) constructs comprising the same (as further described herein).

The advantages that the improved Nanobody of SEQ ID NO:1 and its variants can provide over the Nanobodies described in WO 04/041865 and WO 06/122787 will become clear from the further description herein. For example and without limitation, these advantages may include

- improved stability (such as improved thermal stability as determined by measuring the Tm); and/or
- and/or improved storage stabilty, as for example measured in the SEC experiment described in Example 5); and/or
- a reduced tendency to form dimers under certain formulation conditions (for example, at high concentrations in certain aqueous formulation buffers—see again for example Example 5).

In addition, it has been found that the improved Nanobody of SEQ ID NO:1 and its variants are particularly suited for extending the half-life of immunoglobulin single variable domains that contain more than one disulphide bridge, such as VHH's and Nanobodies belonging to the "VHH-1 class" (which as further described herein may comprise two or even three disulphide bridges). For example and without limitation, it has been found that polypeptides that comprise one or more therapeutic VHH's/Nanobodies of the VHH-1 class and the Nanobody Alb-23 (or an Alb-23 variant) may have better expression levels in certain hosts or host cells (and/or other advantageous properties when it comes to expression, purification and/or production/manufacture generally) than corresponding polypeptides that contain a serum albumin-binding Nanobody according to WO 06/122787 such as "Alb-8" (SEQ ID NO:62 in WO 06/122787) instead of the amino acid sequence of SEQ ID NO:1. Again, this will become clear from the further description and the Experimental Part herein.

These and other advantages, as well as the various aspects, embodiments, uses and applications of the invention, will become clear from the further description herein.

It is known that immunoglobulin single variable domains such as Nanobodies, VHH's, (single) domain antibodies, dAbs, IgNAR domains and microbodies (as for example described in WO 00/29004) can be expressed in a number of host cells and host organisms, such as bacterial cells such as *E. coli*, yeast strains such as *Pichia* and *Saccharomyces*, and various mammalian cells or cell lines. Reference is for example made to EP 0 656 946 and EP 0 698 097, as well as the various published patent applications from Ablynx N.V., such as for example WO 04/041862, WO 2006/122786, WO 2008/020079, WO 2008/142164, WO 2009/068627 or WO 2009/147248.

Similarly, it is known that when one or more immunoglobulin single variable domains that are directed against a therapeutic target are linked to a Nanobody that is directed to (human) serum albumin (such as those described in WO 04/041865 and WO 06/122787) in order to provide a construct that has increased half-life (i.e., compared to the therapeutic domain(s) alone), that the resulting polypeptides and constructs can also be expressed in a number of host cells and host organisms, such as bacterial cells such as *E. coli*, yeast strains such as *Pichia* and *Saccharomyces*, and various mammalian cells or cell lines. Reference is again made to WO 04/041865, WO 06/122787, to WO 2010/056550 and to the various published patent applications from Ablynx N.V. mentioned herein.

It is also generally known all VHH's and Nanobodies contain at least one disulphide bridge, between the cysteine residue at position 22 and the cysteine residue at position 92 (numbering according to Kabat, see the patent applications of Ablynx N.V.).

Although most VHH's contain only this single disulphide bridge, it is also known that some VHH's contain a total of two (or in exceptional cases three) disulphide bridges. For example, a class of VHH's and Nanobodies referred to as the "VHH-1 type" or "VHH-1 class" commonly has a second disulphide bridge between a cysteine residue at position 50 (the first amino acid residue of CDR2) and a cysteine residue present in CDR3 (such VHH's and Nanobodies also often have the sequence motif EREG at positions 44 to 47). Also, some VHH's derived from camels sometimes have a disulphide bridges between a cysteine residue present in CDR1 and a cysteine residue present in CDR3.

Some non-limiting examples of such VHH-1 type Nanobodies (given as illustration only; other VHH-1 type sequences against other targets can be found in some of the other patent applications from Ablynx N.V.) are the sequences P23ILPMP37D5 (SEQ ID NO: 2490) and P12ILPMP80F10 (SEQ ID NO: 1954) from WO 2009/068627; the sequences PMP30A2 (SEQ ID NO:419), PMP31C5 (SEQ ID NO: 413) and PMP30G11 (SEQ ID NO:416) from WO 2008/020079; and the sequences RSVPMP5A2 (SEQ ID NO: 262), RSVPMP5B2 (SEQ ID NO: 263) and RSVPMP5C3 (SEQ ID NO: 264) from WO 2009/147248.

The non-prepublished U.S. applications 61/388,172 (filed Sep. 30, 2010 and entitled "*Biological materials related to c-Met*") and U.S. 61/451,869 (filed Mar. 11, 2011 and entitled "*Biological materials related to c-Met*"), both assigned to Ablynx N.V., describe VHH's and Nanobodies that are directed against the therapeutic target c-Met; and some of these VHH's and Nanobodies (such as 4E09, SEQ ID NO:26 in U.S. 61/451,869 and SEQ ID NO: 12 herein, and some of the variants of 4E09 described in in U.S. 61/451,869) also belong to the VHH-1 class.

U.S. 61/388,172 and U.S. 61/451,869 also describe that such VHH-1 type Nanobodies can be linked to a Nanobody against human serum albumin in order increase its half-life (the Nanobody against human serum albumin used in U.S. 61/388,172 and U.S. 61/451,869 is called "Alb-11" and is given in SEQ ID NO: 5 in U.S. 61/451,869. Alb-11 has the same amino acid sequence as Alb-8, which is SEQ ID NO: 62 in WO 06/122787). An example of such a polypeptide comprising Alb-11 and 4E09 is given in SEQ ID NO: 9 of U.S. 61/451,869.

Although VHH's/Nanobodies of the VHH-1 type (or more generally, VHH's/Nanobodies that contain two or three disulphide bridges), as well as polypeptides and other protein constructs comprising the same (including such polypeptides that further comprise at least one Nanobody against serum albumin in order to provide increased half-life), can be expressed in any suitable host or host organism, it has been found that the expression levels that are obtained for such VHH, Nanobodies, polypeptides or constructs may be signifcantly low(er) than the expression levels that are obtained for similar/comparable VHH's, Nanobodies, polypeptides or constructs that contain VHH's or Nanobodies that do not belong to the VHH-1 class (or more generally, that contain VHH's/Nanobodies with only one disulphide bridge). For example and without limitation, whereas expression levels of more than 0.8 g/l or more (such as 1 g/l or more) can routinely be achieved in *Pichia* for polypeptides that comprise Alb-8 and one or more therapeutic Nanobodies that are not of the VHH-1 type (see again some of the published patent applications of Ablynx N.V.), it has been found that it is difficult to achieve expression levels of more than 0.5 g/l for polypeptides that comprise the anti-c-Met VHH-1 type Nanobody 4E09 (SEQ ID NO:26 in U.S. 61/451,869 and SEQ ID NO: 12 herein) or a humanized variant thereof and Alb-8 (see the Experimental Section below). Surprisingly, it has now been found that when the Nanobody of SEQ ID NO:1 is used in such polypeptides (i.e., instead of Alb-8), that significantly higher expression levels can be obtained (see the Experimental Section below).

As mentioned, in a first aspect, the invention relates to an amino acid sequence that is directed against (human) serum albumin, which essentially consists of or is the following amino acid sequence:

[SEQ ID NO: 1]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSS

This amino acid sequence is also referred to herein as "Alb-23" or the "amino acid sequence of the invention". Alb-23 is a humanized version of the amino acid sequence "Alb-1" (SEQ ID NO: 52 from WO 06/122787, and also referred to in WO 06/122787 as "PMP6A6").

For the sake of convenience, FIG. 1 gives an alignment of Alb-23 with Alb-1 and the humanized versions of Alb-1 disclosed in Table III of WO 06/122787 (called "Alb-3" to "Alb-10" in WO 06/122787, see also SEQ ID NO's: 57 to 64 of WO 06/122787). The amino acid sequence of Alb-1 is:

[SEQ ID NO: 2]
AVQL<u>V</u>ESGGGLVQPG<u>N</u>SLRLSCAASGFTFRSFGMSWVRQAPGK<u>EP</u>EWVSS

ISGSGSDTLYADSVKGRFTISRDN<u>AKT</u>TLYLQMNSL<u>K</u>PEDTAVYYCTIGG

SLSRSSQGTQVTVSS

In the above sequence, the main differences between Alb1 and Alb-23 have been indicated in bold and underlined. These are (with the numbering according to Kabat, see for example Tables A-5 to A-8 of WO 2008/020079; and with each letter denominating an amino acid residue in accordance with the standard one-letter amino acid code, for which reference is made to Table A-2 of WO 2008/020079): position 5: V to L; position 16: N to G; positions 44 and 45: EP to GP; positions 74 to 76: AKT to SKN; position 83: K to R.

Thus, in a further aspect, the invention relates to an amino acid sequence that is a variant of the sequence Alb-1 (SEQ ID NO:2), which variant, comprises:

(i) the amino acid motif GP on positions 44 and 45;
(ii) the amino acid motif SKN on positions 74 to 76;
(iii) a CDR1 that is the amino acid sequence SFGMS (SEQ ID NO:29);
(iv) a CDR2 that is the amino acid sequence SISGSGSDT-LYADSVKG (SEQ ID NO:30);
(v) a CDR3 that is the amino acid sequence GGSLSR (SEQ ID NO:31);
and that preferably also comprises
(vi) a G at position 16;
and in which preferably (but without limitation):
(vii) position 83 is an R (but may optionally also be a K; and that further comprises (i.e., in addition to the aforementioned amino acid differences at positions 16, 44 and 45, 74 to 76 and 83, with the amino acid differences at positions 16 and 83 being optional but preferred) between 1 and 7, such as between 1 and 5 further "amino acid differences" (as defined in WO 2008/020079) with the sequence given in SEQ ID NO:2, which may for example be one or more humanizing substitutions (as defined in WO 2008/020079; see for example again Tables A-5 to A-8) and/or other substitutions (with non-limiting examples of such humanizing or other substitutions being: position 1: A to E, position 14 P to A, or position 108: Q to L).

Similarly, the invention relates to an amino acid sequence that is a variant of the sequence Alb-23 (SEQ ID NO:1), which variant comprises:
(i) the amino acid motif GP on positions 44 and 45;
(ii) the amino acid motif SKN on positions 74 to 76;
(iii) a CDR1 that is the amino acid sequence SFGMS (SEQ ID NO:29);
(iv) a CDR2 that is the amino acid sequence SISGSGSDT-LYADSVKG (SEQ ID NO:30);
(v) a CDR3 that is the amino acid sequence GGSLSR (SEQ ID NO:31);
and that preferably also comprises
(vi) a G at position 16;
and in which preferably (but without limitation):
(vii) position 83 is an R (but may optionally also be a K);
and that further comprises between 1 and 7, such as between 1 and 5 further "amino acid differences" (as defined in WO 2008/020079) with the sequence given in SEQ ID NO:1, which may for example be one or more humanizing substitutions (as defined in WO 2008/020079; see for example again Tables A-5 to A-8) and/or other substitutions (with non-limiting examples of such humanizing or other substitutions being: position 1: A to E, position 14: P to A, or position 108: Q to L).

As will be clear to the skilled person, and although (the use of) Alb-23 is generally preferred within the context of the present invention, the variants described in the preceding paragraphs share with Alb-23 some of the same amino acid substitutions (i.e., compared to Alb-1) that are characteristic of Alb-23 (also compared to the humanized variants of Alb-1 described in WO 06/122787), and thus are expected to provide at least some or even all of the advantages described herein for Alb-23. For these reasons, these variants are also referred to herein as "Alb-23-like sequences" or "Alb-23 variants".

In one specific, but non-limiting aspect, an Alb-23 variant is such that, when it is used in the storage stability assay described in Example 5 (i.e., as part of a construct that further comprises IGE045 and a 9GS linker), that the pre-peak on SE-HPLC for the construct comprising the Alb-23 variant after 1 month storage at 25° C. (under the further conditions given in Example 5) is less than 10%, preferably less than 5%©; and/or that the pre-peak on SE-HPLC for the construct comprising the Alb-23 variant after 1 month storage at 40° C. (under the further conditions given in Example 5) is less than 20%, preferably less than 15%. Reference is for example made to the comparative results in Table 8.

Some non-limiting examples of some Alb-23 like sequences are given in SEQ ID NO's: 3 to 11. The variants of SEQ ID NO's 6 to 11 (or other Alb-23 variants with 1 to 3 amino acid residues at the C-terminus, which may each be independently chosen from naturally occurring amino acid residues and may for example be independently chosen from G, V, L and I) may in particular be used when the albumin-binding Nanobody is provided at the C-terminal end of the polypeptide or protein construct. An alignment of Alb-23 with the sequences of SEQ ID NO's: 6 to 11 is given in FIG. 2.

Alb-23A:
[SEQ ID NO: 3]
AVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSS

Alb-23B:
[SEQ ID NO: 4]
AVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTQVTVSS

Alb-23C:
[SEQ ID NO: 5]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTQVTVSS

Alb-23D:
[SEQ ID NO: 6]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSSA

Alb-23E:
[SEQ ID NO: 7]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSSAA

Alb-23F:
[SEQ ID NO: 8]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSSAAA

Alb-23G:
[SEQ ID NO: 9]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSSG

-continued

Alb-23H:
[SEQ ID NO: 10]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSSGG

Alb-23I:
[SEQ ID NO: 11]
EVQLLESGGGLVQPGGSLRLSCAASGFTFRSFGMSWVRQAPGKGPEWVSS

ISGSGSDTLYADSVKGRFTISRDNSKNTLYLQMNSLRPEDTAVYYCTIGG

SLSRSSQGTLVTVSSGGG

Thus, in one specific, but non-limiting aspect, the invention provides proteins or polypeptides that essentially consist of the amino acid sequence Alb-23 (or of one of the Alb-23 variants described herein).

As further described herein, the amino acid sequence Alb-23 and the further Alb-23 variants described herein can be used with advantage as a moiety, binding unit or fusion partner in order to increase the half-life of therapeutic moieties such as polypeptides, proteins, compounds (including, without limitation, small molecules) or other therapeutic entities.

Thus, in another aspect, the invention provides polypeptides, proteins, constructs, compounds or other chemical entities that comprise or essentially consist of the amino acid sequence Alb-23 (or of one of the Alb-23 variants described herein) and one or more other amino acid sequences, (binding) domains, binding units or other moieties or chemical entities.

In particular, the invention provides polypeptides, proteins, constructs, compounds or other chemical entities that comprise the amino acid sequence Alb-23 (or of one of the Alb-23 variants described herein) and one or more (such as one or two) therapeutic moieties (which may be the same or different, and may for example be directed against the same target or to different targets, and when they are directed to the same target may be directed towards the same or different epitopes, parts, domains or subunits of said target), suitably linked to each other either directly or via one or more suitable linkers or spacers. Such polypeptides, proteins or constructs may for example and without limitation be a fusion protein, as further described herein.

The invention further relates to therapeutic uses of such polypeptides, proteins, constructs or compounds and to pharmaceutical compositions comprising such polypeptides, proteins, constructs or compounds.

In one aspect, the at least one therapeutic moiety comprises or essentially consists of a therapeutic protein, polypeptide, compound, factor or other entity. In a preferred embodiment the therapeutic moiety is directed against a desired antigen or target, is capable of binding to a desired antigen (and in particular capable of specifically binding to a desired antigen), and/or is capable of interacting with a desired target. In another embodiment, the at least one therapeutic moiety comprises or essentially consists of a therapeutic protein or polypeptide. In a further embodiment, the at least one therapeutic moiety comprises or essentially consists of a binding domain or binding unit, such as an immunoglobulin or immunoglobulin sequence (including but not limited to a fragment of an immunoglobulin), such as an antibody or an antibody fragment (including but not limited to an ScFv fragment), or of another suitable protein scaffold, such as protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

In yet another aspect, the at least one therapeutic moiety comprises or essentially consists of an antibody variable domain, such as a heavy chain variable domain or a light chain variable domain.

In a preferred aspect, the at least one therapeutic moiety comprises or essentially consists of at least one immunoglobulin single variable domain, such as a domain antibody, single domain antibody, "dAb" or Nanobody (such as a VHH, a humanized VHH or a camelized VH) or an IgNAR domain.

In a specific embodiment, the at least one therapeutic moiety comprises or essentially consists of at least one monovalent Nanobody or a bivalent, multivalent, bispecific or multispecific Nanobody construct.

The polypeptides, (fusion) proteins, constructs or compounds that comprise Alb-23 (or an Alb-23) variant and one or more therapeutic moieties can generally be (prepared and used) as described in the prior art cited above (such as WO 04/041865 and WO 06/122787), but with Alb-23 or an Alb-23 variant instead of the half-life increasing moieties described in said prior art.

The polypeptides, (fusion) proteins, constructs or compounds that comprise Alb-23 (or an Alb-23) variant and one or more therapeutic moieties will generally and preferably have an increased half-life, compared to the therapeutic moiety or moieties per se.

Generally, the constructs or fusion proteins described herein preferably have a half-life that is at least 1.5 times, preferably at least 2 times, such as at least 5 times, for example at least 10 times or more than 20 times, greater than the half-life of the corresponding therapeutic moiety per se (as measured in either in man or a suitable animal, such as mouse or cynomolgus monkey).

Also, preferably, any such fusion protein or construct has a half-life in man that is increased with more than 1 hour, preferably more than 2 hours, more preferably of more than 6 hours, such as of more than 12 hours, compared to the half-life of the corresponding therapeutic moiety per se.

Also, preferably, any fusion protein or construct has a half-life in man that is more than 1 hour, preferably more than 2 hours, more preferably of more than 6 hours, such as of more than 12 hours, and for example of about one day, two days, one week, two weeks or three weeks, and preferably no more than 2 months, although the latter may be less critical.

Half-life can generally be defined as the time taken for the serum concentration of the polypeptide to be reduce by 50%, in vivo, for example due to degradation of the ligand and/or clearance or sequestration of the ligand by natural mechanisms. In particular, half-life may be as defined in WO 2009/068627.

Methods for pharmacokinetic analysis and determination of half-life are familiar to those skilled in the art. Details may be found in Kenneth, A et al: Chemical Stability of Pharmaceuticals: A Handbook for Pharmacists and in Peters et al, Pharmacokinete analysis: A Practical Approach (1996). Reference is also made to "Pharmacokinetics", M Gibaldi & D Perron, published by Marcel Dekker, 2nd revised edition (1982).

As mentioned, in one aspect, the amino acid sequence Alb-23 (or of one of the Alb-23 variants described herein)

can be used to increase the half-life of (one or more) immunoglobulin single variable domains, such as domain antibodies, single domain antibodies, "dAh's", VHH's or Nanobodies (such as VHH's, humanized VHH's or camelized VH's such as camelized human VH's).

In particular, as mentioned herein, the amino acid sequence Alb-23 (or of one of the Alb-23 variants described herein) can be used with advantage to increase the half-life of immunoglobulin single variable domains that comprise two or more (such as two or three) disulphide bridges, such as VHH's/Nanobodies of the VHH-1 class.

Thus, one embodiment of the invention relates to a polypeptide, construct or fusion protein that comprises the amino acid sequence Alb-23 (or one of the Alb-23 variants described herein) and one or more (such as one or two) immunoglobulin single variable domain sequences, which are suitably linked to each other, either directly or optionally via one or more suitable linkers or spacers. As mentioned herein, each such immunoglobulin single variable domain present in such a polypeptide, construct or fusion protein may independently be a domain antibody, single domain antibody, "dAb'" or Nanobody (such as a VHH, humanized VHH or camelized VH, such as a camelized human VH); and according to one specific but non-limiting aspect, at least one (and up to all) of these immunoglobulin single variable domains comprises two or three disulphide bridges.

Preferably, each such immunoglobulin single variable domain is a Nanobody; and according to one specific but non-limiting aspect, at least one (and up to all) of these immunoglobulin single variable domains is a Nanobody of the VHH-1 class.

For example and without limitation, such a construct, fusion protein or polypeptide may comprise:

one copy of Alb-23 (or of one of the Alb-23 variants described herein) and one such immunoglobulin single variable domain sequence;

one copy of Alb-23 (or of one of the Alb-23 variants described herein) and two such immunoglobulin single variable domain sequences (which may be the same or different);

or even (although usually not required and less preferred because the resulting protein is bigger)

two copies of Alb-23 (or two copies of the Alb-23 variants described herein, which may be the same or different) and one such immunoglobulin single variable domain sequence;

two copies of Alb-23 (or two copies of the Alb-23 variants described herein, which may be the same or different) and two such immunoglobulin single variable domain sequence (which may be the same or different);

one copy of Alb-23 and three such immunoglobulin single variable domain sequence (which may be the same or different).

Some non-limiting examples of constructs, fusion proteins or polypeptides of the invention can be schematically represented as follows, in which "[Alb-23]" represents Alb-23 (or of one of the Alb-23 variants described herein), "[therapeutic moiety 1]" and "[therapeutic moiety 2]" represent the therapeutic moieties (which as mentioned may each independently be an immunoglobulin single variable domain), "-" represents a suitable linker (which is optional) and the N-terminus is on the left hand side and the C-terminus is on the right hand side:

[Alb-23] - [therapeutic moiety 1]
[therapeutic moiety 1] - [Alb-23]
[Alb-23] - [therapeutic moiety 1] - [therapeutic moiety 1]
[therapeutic moiety 1] - [therapeutic moiety 1] - [Alb-23]
[therapeutic moiety 1] - [Alb-23] - [therapeutic moiety 1]
[Alb-23] - [therapeutic moiety 1] - [therapeutic moiety 2]
[therapeutic moiety 1] - [therapeutic moiety 2] - [Alb-23]
[therapeutic moiety 1] - [Alb-23] - [therapeutic moiety 2]

When two or more different therapeutic moieties (such as two or more different immunoglobulin single variable domains) are present in the constructs or polypeptides of the invention, they may be the same or different, and when they are different they may be directed towards the same target (for example, to the same or different parts, domains, subunits or epitopes of said target) or to different targets.

Thus, in another aspect, the invention relates to a multispecific (and in particular bispecific) Nanobody construct that comprises Alb-23 (or of one of the Alb-23 variants described herein) and at least one other Nanobody (such as one or two other Nanobodies, which may be the same or different), in which said at least one other Nanobody is preferably directed against a desired target (which is preferably a therapeutic target) and/or another Nanobody that useful or suitable for therapeutic, prophylactic and/or diagnostic purposes. Again, Alb-23 and the other Nanobodies may be suitably linked to each other either directly or optionally via one or more suitable linkers or spacers, and according to one specific but non-limiting aspect at least one (and up to all) of the other Nanobodies may be of the VHH-1 class.

For a general description of multivalent and multispecific polypeptides containing one or more Nanobodies and their preparation, reference is also made to Conrath et al., J. Biol. Chem., Vol. 276, 10. 7346-7350, 2001; Muyldennans. Reviews in Molecular Biotechnology 74 (2001), 277-302; as well as to for example WO 96/34103, WO 99/23221, WO 04/041862, WO 2006/122786, WO 2008/020079, WO 2008/142164 or WO 2009/068627.

Some other examples of some specific multispecific and/or multivalent polypeptide of the invention can be found in the applications by Ablynx N.V. mentioned herein. In particular, for a general description of multivalent and multispecific constructs comprising at least one Nanobody against a serum protein for increasing the half-life, of nucleic acids encoding the same, of compositions comprising the same, of the preparation of the aforementioned, and of uses of the aforementioned, reference is made to the International applications WO 04/041865 and WO 06/122787 mentioned above (Alb-23 and the Alb-23 variants described herein can generally be used analogously to the half-life extending Nanobodies described therein such as Alb-8), as well as to the general description and specific examples of such constructs given in WO 04/041862, WO 2006/122786, WO 2008/020079, WO 2008/142164 or WO 2009/068627.

In one non-limiting embodiment, the one or more other Nanobodies present in such a polypeptide or protein construct may be directed against c-Met, and may in particular be Type I Nanobodies directed against c-Met. Some non-limiting examples of Nanobodies against c-Met that may be present in such a polypeptide or protein construct may for example be found in the non-prepublished U.S. applications U.S. 61/388,172 and U.S. 61/451,869 mentioned herein.

One particularly preferred Type I Nanobody against c-Met that may be present in such a multivalent and/or multispecific polypeptide (next to Alb-23 or an Alb-23 variant) is 4E09 (SEQ ID NO:26 in U.S. 61/451,869 and SEQ ID NO: 12 herein) or variant thereof. Such a variant of 4E09 may generally be as described in U.S. 61/451,869 (and will generally have at least 80%, such as at least 85%, for example at least 90% or more such as 95% or more sequence identity with 4E09) and is preferably such that (i) it competes with 4E09 for binding to c-Met (in a suitable binding assay, such as the alphascreen assay described in Example 7, but using 4E09 instead of HGF as used in Example 7); and/or (ii) it binds to the same epitope on c-Met as 4E09; and/or (iii) cross-blocks (as defined in WO 2009/068627) the binding of 4E09 to c-Met. Such a variant of 4E09 may for example be a humanized and/or sequence-optimized variant of 4E09 (as further described in U.S. 61/451,869). Some preferred, but non-limiting examples of variants of 4E09 that could be present in such proteins or polypeptides are the following, which are also described in U.S. 61/451, 869: 04E09 (L49S); 04E09 (C50S/C100bG); 04E09 (C22A/C92S); A00790067=4E09 (Q108L); A00790068=4E09 (A74S, K83R, Q108L); A00790069=4E09 (A74S, K83R, G88A, Q108L) and A00790105=4E09 (E1D, A74S, K83R, G88A, Q108L), of which the latter is especially preferred. The amino acid sequences of 4E09 and these variants are given in SEQ ID NO's: 12 to 19.

Thus, in one specific but non-limiting aspect, the invention relates to a polypeptide or protein construct that comprises or essentially consists of Alb-23 (preferred) or an Alb-23 variant (as described herein), which is suitably linked (either directly or via one or more suitable linkers) to one or two Nanobodies against c-Met. As mentioned, according to a specific but non-limiting aspect, said one or two Nanobodies against c-Met comprise two disulphide bridges (i.e. are of "Class I").

In particular, the invention relates to a polypeptide or protein construct that comprises or essentially consists of Alb-23 (preferred) or an Alb-23 variant (as described herein), which is suitably linked (either directly or via one or more suitable linkers) to one or two (and preferably only one) Nanobodies against c-Met, which are 4E09 (SEQ ID NO 12) or a variant of 4E09 (as described herein and in U.S. 61/451,869), and preferably a humanized or sequence optimized variant of 4E09 and more preferably A00790105 (SEQ ID NO: 19).

Some specific but non-limiting examples of such proteins and polypeptides are the constructs Alb23-9GS-4E09, 4E09-9GS-Alb23, Alb23-9GS-A00790105, A00790105-9GS-Alb23, Alb23-35GS-4E09, 4E09-35GS-Alb23, Alb23-35GS-A00790105, A00790105-35GS-Alb23, and A00790105-35GS-A00790105-35GS-Alb23. The sequences of these are given in SEQ ID NO's: 20 to 28, respectively. Of these, the construct A00790105-9GS-Alb23 (SEQ ID NO: 23) is particularly preferred, and thus one aspect of the invention also relates to a polypeptide that has at least 80%, such as at least 85%, for example at least 90%, such as at least 95% or more sequence identity with the polypeptide of SEQ ID NO: 23.

The invention also relates to nucleotide sequences or nucleic acids that encode amino acid sequences, fusion proteins and constructs described herein. The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V. such as for example WO 04/041862, WO 2006/122786, WO 2008/020079, WO 2008/142164 or WO 2009/068627.

The invention also relates to hosts or host cells that contain such nucleotide sequences or nucleic acids, and/or that express (or are capable of expressing), the amino acid sequences, fusion proteins and constructs described herein. Again, such host cells can be generally as described in the published patent applications of Ablynx N.V., such as for example WO 04/041862, WO 2006/122786, WO 2008/020079, WO 2008/142164 or WO 2009/068627.

The invention also relates to a method for preparing an amino acid sequence, fusion protein or construct as described herein, which method comprises cultivating or maintaining a host cell as described herein under conditions such that said host cell produces or expresses an amino acid sequence, fusion protein or construct as described herein, and optionally further comprises isolating the amino acid sequence, fusion protein or construct so produced. Again, such methods can be performed as generally described in the published patent applications of Ablynx N.V., such as for example WO 04/041862, WO 2006/122786, WO 2008/020079, WO 2008/142164 or WO 2009/068627.

The invention also relates to a pharmaceutical composition that comprises at least one amino acid sequence, fusion protein or construct as described herein, and optionally at least one pharmaceutically acceptable carrier, diluent or excipient. Such preparations, carriers, excipients and diluents may generally be as described in the published patent applications of Ablynx N.V., such as for example WO 04/041862, WO 2006/122786, WO 2008/020079. WO 2008/142164 or WO 2009/068627.

However, since the amino acid sequences, fusion proteins or constructs described herein have an increased half-life, they are preferably administered to the circulation. As such, they can be administered in any suitable manner that allows the amino acid sequences, fusion proteins or constructs to enter the circulation, such as intravenously, via injection or infusion, or in any other suitable manner (including oral administration, subcutaneous administration, intramuscular administration, administration through the skin, intranasal administration, administration via the lungs, etc.) that allows the amino acid sequences, fusion proteins or constructs to enter the circulation. Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

Thus, in another aspect, the invention relates to a method for the prevention and/or treatment of at least one disease or disorder that can be prevented or treated by the use of a fusion protein or construct as described herein, which method comprises administering, to a subject in need thereof, a pharmaceutically active amount of a fusion protein or construct of the invention, and/or of a pharmaceutical composition comprising the same. The diseases and disorders that can be prevented or treated by the use of a fusion protein or construct as described herein will generally be the same as the diseases and disorders that can be prevented or treated by the use of the therapeutic moiety that is present in the fusion protein or construct of the invention.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a fusion protein or construct of the invention, and/or of a pharmaceutical composition comprising the same.

The fusion protein or construct and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more fusion proteins or constructs of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency and/or the half-life of the specific fusion proteins or constructs to be used, the specific route of administration and the specific pharmaceutical formulation or composition used, the Nanobodies and polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Usually, in the above method, a single polypeptide of the invention will be used. It is however within the scope of the invention to use two or more polypeptides of the invention in combination.

The polypeptides of the invention may also be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides of the invention may be used in combination with other pharmaceutically active compounds or principles that are or can be used for the prevention and/or treatment of the diseases and disorders that can be prevented or treated with the fusion proteins or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, in particular a mammal, and more in particular a human being. As will be clear to the skilled person, the subject to be treated will in particular be a person suffering from, or at risk from, the diseases and disorders mentioned herein.

Other aspects, embodiments, advantages and applications of the invention will become clear from the further description herein.

The invention will now be further illustrated by means of the non-limiting Experimental Part and Figures, in which:

FIG. 2 is an alignment of Alb-23 (SEQ ID NO: with some of the Alb-23 variants described herein:

FIG. 3 shows the various sequences referred to in the present specification;

FIG. 5 shows an expression profile using SDS-PAGE analysis of A007900171 produced by *Pichia* clones with a low (L=1) and high (H=more than 1) copy number (CN) of the expression cassette.

Figure 8:
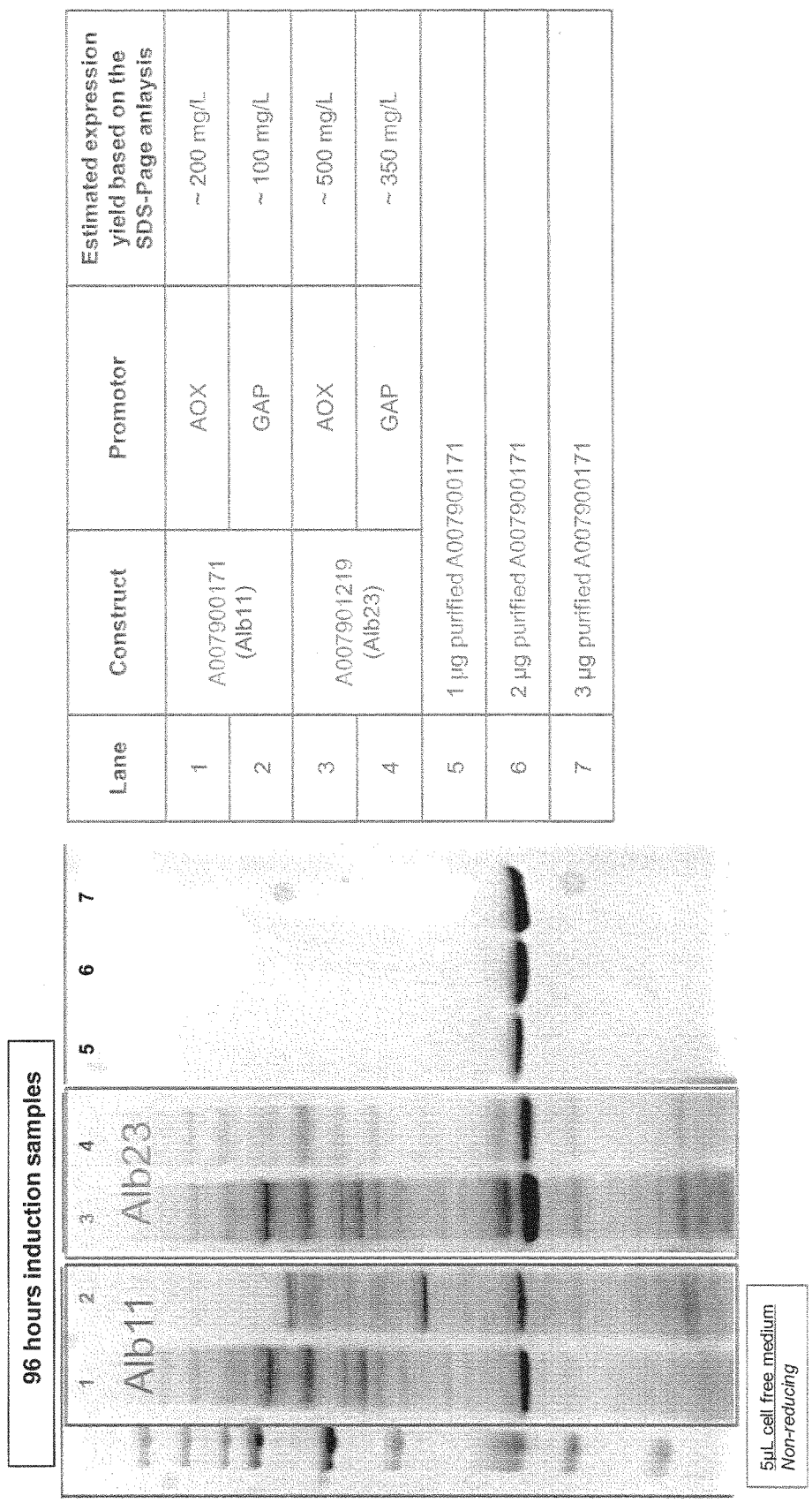

FIG. 8 shows SDS-Page analysis (non-reducing conditions) of end of induction fermentation samples of *Pichia pastoris* expressions of A00700171 and A00701219. 5 μL cell free medium is loaded onto the gel (Lane 1-4). Lanes 5 to 7 contain a control Nanobody loaded in different amounts. Left lane contains the molecular weight marker.

EXPERIMENTAL PART

Example 1

Expression Profile of 4E09 in Combination with Alb11 or Alb23

Figure 1:
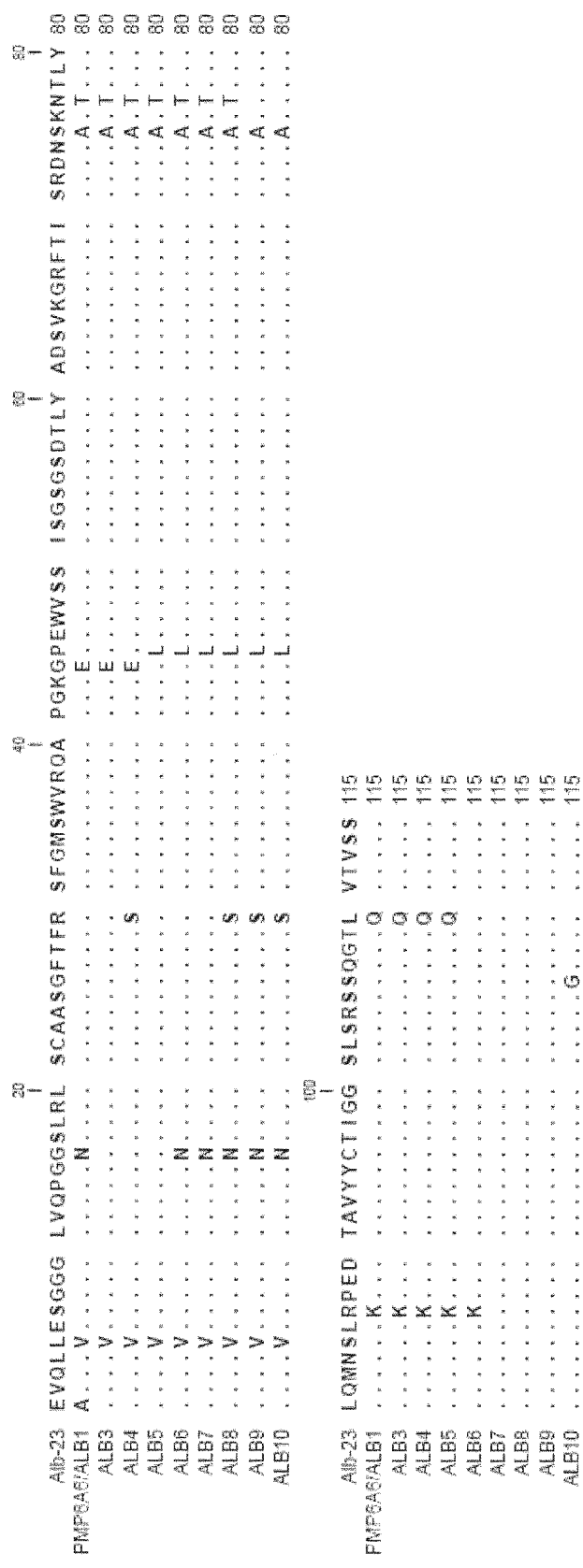
FIG. 1 is an alignment of Alb-23 (SEQ ID NO: 1) with Alb-1 and the various humanized variants thereof described in WO 06/122787.
Figure 4:
FIG. 4 shows an expression profile using SDS-PAGE analysis of A007900009 produced by *Pichia* clones with a low (L=1) and high (H more than 1) copy number (CN) of the expression cassette.
Figure 5:
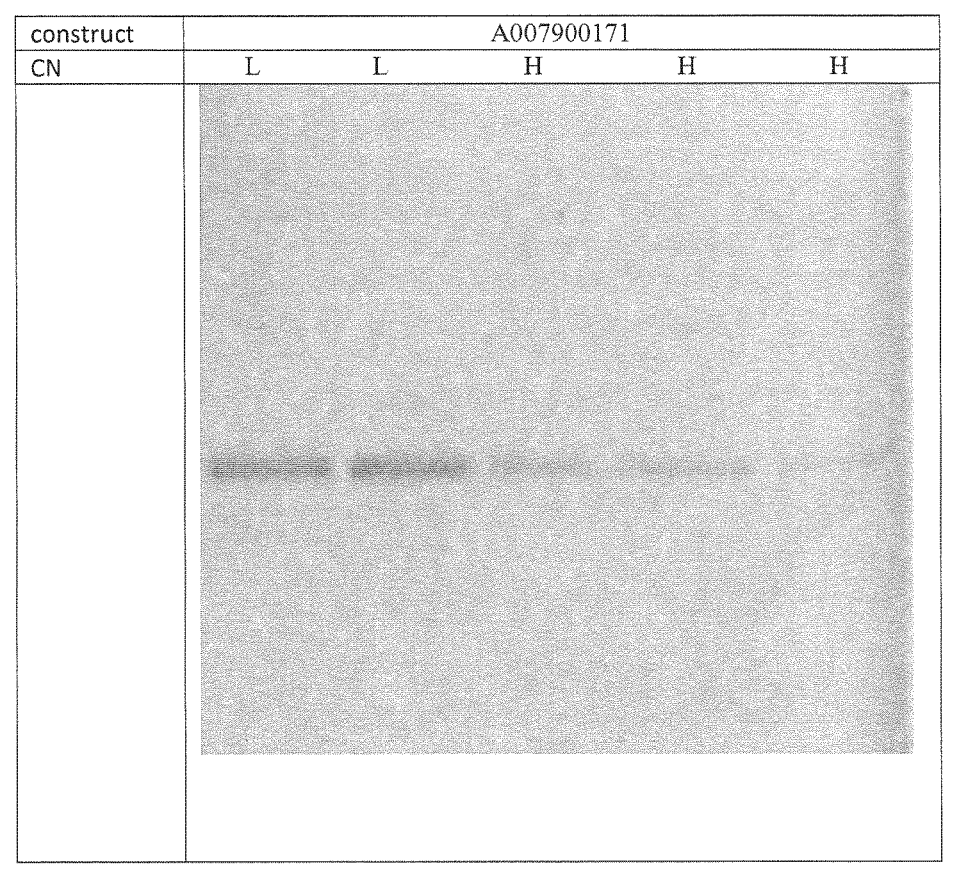
Figure 6:
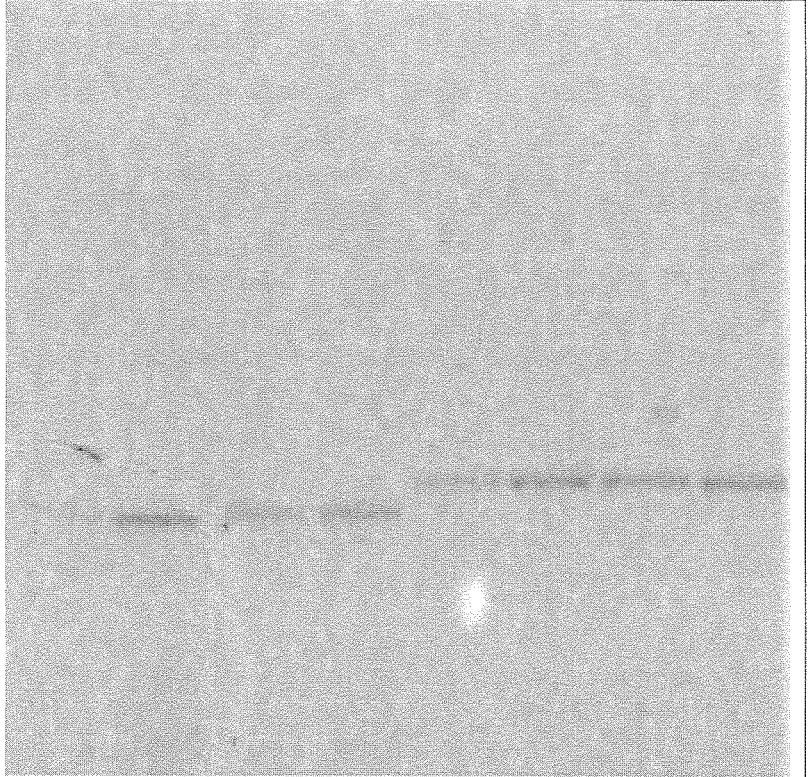
FIG. 6 shows an expression profile using SDS-PAGE analysis of A007900057 and A007900058 produced by *Pichia* clones with a low (L=1) and high (H=more than 1) copy number (CN) of the expression cassette.
Figure 7:
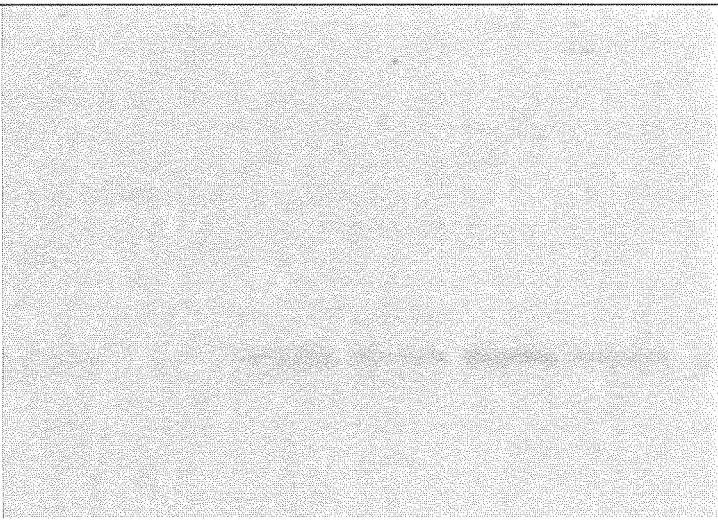
FIG. 7 shows an expression profile using SDS-PAGE analysis of A007901219 variant produced by *Pichia* clones with a low (L=1) and high (H=more than 1) copy number (CN) of the expression cassette.

Table 1 gives an overview of the formats based on the anti-c-Met 4E09 VHH1 Nanobody building block (SEQ ID NO:12) in combination with Alb11 and Alb23. The different Nanobodies were cloned into the pPiczalpha expression vector and transformed in *Pichia pastoris* X-33 strain (commercially available expression system from Invitrogen/ RCT), Clones were selected on zeocin containing plates and a qPCR was performed to rank the clones according to their copy numbers. Expression levels were compared between low and high copy number clones in shake flask experiments. An inverse correlation between expression level and copy numbers was observed for Alb11 containing formats (FIGS. 4 and 5). In contrast, a positive correlation between expression level and copy numbers was observed with Nanobody formats containing the Alb23 Nanobody (FIGS. 6 and 7).

TABLE 1

Overview of 5 formats of the VHH1 4E09 Nanobody building block or sequence optimized version fused via a 9GS or 35GS linker to the Alb11 or Alb23 Nanobody building block.

| Format | Construct | SEQ ID NO: |
|---|---|---|
| A007900009 | 4E09-9GS-ALB11-Flag3-His6 | 39 |
| A007900057 | 4E09-9GS-ALB23 | 21 |
| A007900058 | 4E09-35GS-ALB23 | 25 |
| A007900171 | A00790105 -9GS-Alb11 | 40 |
| A007901219 | A00790105- -9GS-Alb23 | 23 |

Example 2

Fermentation Yield of 4E09 in Combination with Alb11 or Alb23

Expression of the A007900171 (4E9 sequence optimized-9GS-Alb11) and A007901219 (4E9 sequence optimized-9GS-Alb23) Nanobody® was evaluated using *Pichia pastoris* X33 as host organism. Both the AOX promoter (MeOH inducible promoter) and GAP promoter (constitutive induced promoter) were evaluated.

A complex, peptone based medium was used for the fermentation processes. For the fermentations with the X33 clone using the AOX promoter, MeOH was used for expression of the Nanobody. In short, this process can be divided in 3 phases: a batch phase, a glycerol fed batch and a MeOH induction phase. During the batch and glycerol fed batch phase, biomass was build up to approx. 40% (wet weight per volume). Then a MeOH adaptation and induction phase was started during which the Nanobody® was expressed and secreted into the medium.

For the fermentations with the X33 clone using the GAP promoter, glucose was used to induce expression of the Nanobody®. This process can also be divided in 3 phases: a batch phase on glycerol, a glucose fed batch using a high feed rate to build-up biomass to approx. 40° A (wet weight per volume) and a second glucose fed batch phase at a lower feed rate to further induce expression/secretion of the Nanobody®.

All Fermentations were carried out at 2L fermenter scale using Sartorius equipment (Biostat® Aplus, Biostat® Bplus and Biostat® Bplus twin controllers, 2L Univessel® reactors, control via MFCSwin software). During fermentations the following parameters were monitored/steered: DO (dissolved oxygen), pH, foaming, biomass ($OD_{600}$ for *E. coli* and Wet Cell Weight (WCW) for *Pichia pastoris*), expression level and quality of the product. The DO was typical 30% and controlled via a stirring cascade, and further compensated by addition of pure oxygen on a need basis. The pH was monitored via a pH electrode and adjusted via ammonia additions via a base pump. Off line pH measurements were done to check pH electrode functioning following autoclaving.

Table 2 gives an overview of the fermentation runs performed for expression of A007900171 and A007901219 using *Pichia pastoris* as host organism.

FIG. 8 shows the SDS-Page analysis (non-reducing conditions) of the end of induction samples of the different fermentations with *Pichia pastoris*.]

In Table 3 an overview of the different *Pichia pastoris* fermentations with their respective parameter settings, fermentation characteristics, and the estimated expression yield of the end of induction samples based on SDS-Page analysis, is shown.

The titer and purity of the produced Nanobody® at end of fermentation was determined via a small scale protA clean-up procedure followed by RP-HPLC analysis. In short, sample preparation is based on protA affinity chromatography which purifies the Nanobody® from the medium. The protein concentration of the elution fraction is determined using UV spectrophotometry and is followed by Reversed Phase High Performance Liquid Chromatography (RP-HPLC) allowing determination of product titer and product purity/heterogeneity. Table 4 summarizes the RPC results.

TABLE 2

Overview of the fermentation runs performed for expression of A007900171 and A007901219 using *P. pastoris* as host organism

| Fermentation ID | Construct | Strain | Promoter | Fed-batch | Fed-batch feed rate | Induction | Induction feed rate |
|---|---|---|---|---|---|---|---|
| A1/110511 | A007901219 Alb23 | X33 | AOX | 60% glycerol + 10% peptone | 21.6 g/h · 1 | 100% MeOH | 3.16 g/h · 1 |

TABLE 2-continued

Overview of the fermentation runs performed for expression of A007900171 and A007901219 using *P. pastoris* as host organism

| Fermentation ID | Construct | Strain | Promoter | Fed-batch | Fed-batch feed rate | Induction | Induction feed rate |
|---|---|---|---|---|---|---|---|
| A1/110518 | A007900171 Alb11 | X33 | AOX | 60% glycerol + 10% peptone | 21.6 g/h · l | 100% MeOH | 3.16 g/h · l |
| A2/110511 | A007901219 Alb23 | X33 | GAP | 25% glucose + 5% peptone | 50.8 g/h · l | 50% glucose | 6 g/h · l |
| A4/110511 | A007900171 Alb11 | X33 | GAP | 25% glucose + 5% peptone | 50.8 g/h · l | 50% glucose | 6 g/h · l |

TABLE 3

Overview of the different A007900035 fermentations with *Pichia pastoris* and their respective expression yield in clarified medium at end of fermentation determined via SDS-Page analysis.

| Fermentation ID | Construct | Strain | Promoter | Induction time | WCW at end of induction (g/L) | Expression yield (mg/L clarified medium) | Expression yield (mg/L broth) |
|---|---|---|---|---|---|---|---|
| A1/110511 | A007901219 Alb23 | X33 | AOX | 95 hrs | 420 g/L | ~500 mg/L | ~290 mg/L |
| A1/110518 | A007900171 Alb11 | X33 | AOX | 92 hrs | 423 g/L | ~200 mg/L | ~115 mg/L |
| A2/110511 | A007901219 Alb23 | X33 | GAP | 91 hrs | 421 g/L | ~350 mg/L | ~203 mg/L |
| A4/110511 | A007900171 Alb11 | X33 | GAP | 93 hrs | 374 g/L | ~100 mg/L | ~63 mg/L |

TABLE 4

Overview of the total yield determined via $OD_{280}$ and RPC analysis after a ProtA clean-up step, % main peak and the intact monomeric yield. All yields are expressed in mg/L cell free medium.

| Ferm. ID | Construct | Promoter | Total Yield via $OD_{290}$ after ProtA clean-up | Total Yield via RPC analysis after ProtA clean-up | % Main peak (RPC analysis) | Intact yield via RPC analysis after ProtA clean-up |
|---|---|---|---|---|---|---|
| A1/110511 | A007901219 Alb23 | AOX | 820 mg/L | 670 mg/L | 68.7% | 460 mg/L |
| A1/110518 | A007900171 Alb11 | AOX | 250 mg/L | 200 mg/L | 88.0% | 170 mg/L |
| A2/110511 | A007901219 Alb23 | GAP | 340 mg/L | 290 mg/L | 79.0% | 230 mg/L |
| A4/110511 | A007900171 Alb11 | GAP | 180 mg/L | 150 mg/L | 86.0% | 130 mg/L |

Example 3

Purification of A007900171 and A007901219

Both A007900171 and A007901219 molecules were purified according to the scheme shown in Table 5:

TABLE 5

Overview of purification steps.

| Process | Description | Aim |
|---|---|---|
| Step 1: Clarification | Centrifugation and TFF microfiltration (0.2 μm Hydrosart Sartocon slice cassette, Sartorius) | Clarification of the fermentation broth |
| Step 2: Capture step | HCIC (MEP Hypercel with elution at pH 3.5 + neutralization with 25 mM Tris pH 8.5) + buffer exchange* (Sephadex G25 to 25 mM Tris buffer pH 8.5) | Capture product from the medium and removal of impurities |
| Step 3: Intermediate step | AIEX (POROS 50HQ or Q Sepharose HP) in 25 mM Tris pH 8.5 | Removal of product related variants and impurities |
| Step 4: Polish step | OGP treatment for LPS removal + SEC (Superdex 75) | Removal of LPS and product related variants and impurities |

*Only for A007901219

Example 4

Comparison of Properties of Alb-1, Alb-8 (=Alb-11) and Alb-23

Various properties of Alb-1, Alb-8 and Alb-23 were determined and compared. The results are shown in Table 6.

Also, for a side-by-side comparison of the tendency of Alb-8 and Alb-23 to form dimers, dimerization kinetics for monovalent Alb-8 (Ea=73.0 kcal/mol) and Alb-23 (Ea=50.8 kcal/mol) at various temperatures in PBS buffer were calculated from an Arrhenius plot. The results are shown in Table 7, and show that for Alb-11, the kinetics start to increase from room temperature upwards, in particular when compared to Alb-23.

TABLE 6

Comparison of some of the properties of Alb-1, Alb-8 and Alb-23.

|  |  | ALB1 | ALB23 | ALB8 |
|---|---|---|---|---|
| $K_D$ (nM) | Human SA | 1.8 | 2.7 | 4.5 |
|  | Cyno SA | 1.9 | 3.0 | 4.6 |
|  | Murine SA | 17.3 | 16.5 | 68.8 |
| Tm (° C.) | TSA | 64.5 | 69.0 | 61.6 |
|  | DSC | 65.6 | 71.7 | 65.9 |
| Reversibility of unfolding (%) | DSC @ 0.3 mg/ml & Tm + 5° C. | 64 | 92 | 16 |
| Dimerization (%) | 3 w @ 37° C. & 20 mg/ml |  | 2 | 17 |
|  | 12 w @ 37° C. & 20 mg/ml | 6 | 9 | 44 |
| Humanization | % FR identity | 86.5 | 93.3 | 91.0 | a trivalent bispecific Nanobody construct comprising Alb-11 and two Nanobodies against OX40L (see SEQ ID NO:229 of PCT/EP2010/069606 of Ablynx N.V., filed on 14. Dec. 2010) and OX40L089 (SEQ ID NO:45), a corresponding construct comprising the same two Nanobodies against OX40L, but with Alb-23 instead of Alb-11. The results are also shown in Table 8A.

TABLE 8A

Comparative storage stability of Alb-23 and Alb-11 constructs (% Pre peak on SE-HPLC after storage for the indicated storage period at the indicated temperatures)

| Construct | Albumin binder | Storage period | Temperature (° C.) | | | |
|---|---|---|---|---|---|---|
| | | | 4 | 5 | 25 | 40 |
| IGE045-9GS-ALB23 (SEQ ID NO: 41) | Alb-23 | 1 month | — | 0.0 | 3.7 | 7.6 |
| IGE045-9GS-ALB11 (SEQ ID NO: 42) | Alb-11 | 1 month | — | 0.0 | 11.7 | 30.3 |
| OX40L079 (SEQ ID NO: 44) | Alb-11 | 2 weeks | 0.4 | — | 1.4 | 25 |
| OX40L089 (SEQ ID NO: 45) | Alb-23 | 2 weeks | 0.3 | — | 1.4 | 13 |

TABLE 7

Side-by-side comparison of dimerization kinetics of monovalent ALB8/ALB11 and ALB23 over a broad concentration range, as calculated from an Arrhenius plot (max. predicted % dimers after 3 years at the indicated concentration in PBS buffer and indicated temperature).

| | Conc. (mg/ml) | | | | | |
|---|---|---|---|---|---|---|
| | 10 mg/ml | | 25 mg/ml | | 50 mg/ml | |
| Temp (° C.) | ALB11 % dimers | ALB23 % dimers | ALB11 % dimers | ALB23 % dimers | ALB11 % dimers | ALB23 % dimers |
| 5 | 0.00 | 0.03 | 0.01 | 0.09 | 0.02 | 0.17 |
| 10 | 0.04 | 0.15 | 0.09 | 0.37 | 0.18 | 0.74 |
| 15 | 0.31 | 0.63 | 0.77 | 1.60 | 1.50 | 3.20 |
| 20 | 2.50 | 2.70 | 6.30 | 6.60 | 12.50 | 13.30 |
| 25 | 19.00 | 10.60 | 47.50 | 26.60 | 95.10 | 53.20 |
| 30 | >100 | 41.60 | >100 | >100 | >100 | >100 |

Example 5

Storage Stability of Constructs Comprising Alb-23 Compared to Alb-11

To compare the storage stability of bispecific constructs comprising Alb-8 and Alb-23, respectively, two bispecific Nanobody constructs comprising the same Nanobody against IgE (IGE045, SEQ ID NO:43) linked to Alb-23 (IGE045-9GS-ALB23; SEQ ID NO: 41) and Alb-11 (IGE045-9GS-ALB11; SEQ ID NO: 42) were prepared, formulated in D-PBS buffer at a concentration of 50 mg/ml and stored in plastic PCR tubes in the dark for 1 month at different temperatures. After that, the amount of pre-peak (corresponding to dimer formation) was determined and compared using SE-HPLC. The SE-HPLC analysis was performed using aBioSep SEC-2000 column (Phenomenex) and D-PBS as running buffer at a flow rate of 0.2 ml/min. 10 µg material was injected and data was analysed using Chromeleon software. The results are shown in Table 8.

In a similar experiment, the storage stability of two trivalent bispecific constructs were compared (at a concentration of 50 mg/ml in 20 mM His buffer, pH6.5, 8% sucrose). The constructs were OX40L079 (SEQ ID NO:44), In another experiment, the fermentation yield storage stability of four different Nanobody constructs against c-Met (A007901222/SEQ ID NO: 46; A007901256/SEQ ID NO: 47; A007901259/SEQ ID NO: 48 and A007901260/SEQ ID NO: 49) was compared. Of these constructs, A007901222 contains the Alb-23 albumin-binding Nanobody (invention) as well as a "VHH-1 type" anti-c-Met Nanobody (4E09—see again the U.S. applications 61/388,172 and U.S. 61/451,869 referred to above) whereas the other constructs (used as comparative references) contain the Alb-11 albumin-binding Nanobody and anti c-Met Nanobodies which are not of the VHH-1 type. For a more detailed description of the constructs used, reference is made to the co-pending U.S. application Ser. No. 13/435,567 (Beste et al.) by Applicant filed on Mar. 30, 2012.

The different Nanobody constructs were produced in *Pichia pastoris* (see again U.S. Ser. No. 13/435,567, U.S. 61/388,172 and U.S. 61/451,869) and afforded broadly comparable fermentation yields (1.03 g/L for; L43 g/L for A007901256; 0.91 g/L for A007901259 and 1.45 g/L for A007901260), confirming that the present invention makes it possible to provide constructs comprising VHH-1 type Nanobodies with expression yields that are comparable to the expression yields of constructs that do not contain a VHH-1 type Nanobody.

The Nanobody constructs were then purified (>99% purity on SEC and >90% purity on RPC) and incubated at −70° C., −20° C., 5° C., 25° C. and 40° C. at a concentration of about 15 mg/ml in D-PBS for 7.5 weeks. The samples were evaluated by turbidity measurement (OD500), RP-HLPC and SE-HLPC. The results are summarized in Table 8B. Stability was acceptable for all samples tested when stored at −70° C., −20° C. or 5° C. for 7.5 weeks.

TABLE 8B comparative storage stability of different
anti c-Met Nanobody constructs

| Construct | Storage stability (7.5 weeks incubation) | |
|---|---|---|
| | 25° C. | 40° C. |
| A007901222 | 0.3% HMW; OD500 < 0.005 | 3.5% HMW; OD500 = 0.005 |
| A007901256 | 0.5% HMW; OD500 < 0.005 | 24.1% HMW; OD500 = 1.30 (*) |
| A007901259 | 0.7% HMW; OD500 < 0.005 | 23.7% HMW; OD500 = 1.91 (*) |
| A007901260 | 0.5% HMW; OD500 < 0.005 | 23.1% HMW; OD500 = 0.45 (*) |

HMW = high molecular weight (pre-peak) components bilization run at a flow rate of 5 μl/min. Surfaces were first activated with a 7 min injection of a 1:1 mixture of 75 mg/ml EDC and 11.5 mg/ml NHS (Biacore amine coupling kit). Serum albumin was injected at 10 μg/ml in 10 mM acetate pH4.5, until a level of 970RU (flow cell 2), 890RU (flow cell 3) and 1360RU (flowcell 4) for respectively human, cynomolgus and mouse serum albumin was reached. After immobilization, surfaces were deactivated with a 7 min injection of 1M ethanolamine pH8.5. A blank reference surface (flowcell 1) was activated and deactivated as described above. A series of Nanobody concentrations was prepared in HBS-EP+ (i.e. 0 nM, 1.9 nM, 7.8 nM, 31.25 nM, 125 nM, 500 nM, 0 nM, 7.8 nM, 125 nM), were injected for 2 min at 45 μl/min (flow path 1, 2, 3, and 4) and allowed to dissociate in running buffer for 10 min. Between different samples, the surfaces were regenerated with regeneration buffer 10 mM glycine-HCl pH1.5, 100 s at 45 μl/min. Data were double referenced by subtraction of the curves on the reference channel and of a blank running buffer injection curve. Processed curves were evaluated by fitting a 1:1 binding model onto the binding curves in the Biacore T100 Evaluation software. On-rates (ka), off-rates (kd) and affinities (KD) were reported and are shown in Table 9.

TABLE 9

Affinity determination of Nanobodies against serum albumin by surface plasmon resonance (SPR) measurement

| ID | human serum albumin | | | cynomolgus serum albumin | | | mouse serum albumin | | |
|---|---|---|---|---|---|---|---|---|---|
| | $k_{on}$ | $k_{off}$ | $K_D$ | $k_{on}$ | $k_{off}$ | $K_D$ | $k_{on}$ | $k_{off}$ | $K_D$ |
| Alb11 | 5.2 | 1.9 | 3.6 | 4.6 | 1.7 | 3.6 | 7.1 | 35 | 49 |
| A007900171 (Alb11)* | 1.0 | 6.2 | 60 | 0.93 | 6.1 | 66 | 0.93 | 66 | 710 |
| Alb23 | 4.5 | 1.2 | 2.6 | 4.0 | 1.1 | 2.7 | 7.0 | 12 | 17 |
| A007901219 (Alb23) | 1.3 | 3.3 | 24 | 1.2 | 3.2 | 27 | 1.7 | 50 | 300 |

$k_{on}$ is given in $10^5$ $M^{-1}s^{-1}$,
$k_{off}$ is given in $10^{-3}$ $s^{-1}$,
$K_D$ is given in nM ($10^{-9}$M)
*Data obtained in a separate but equivalent experiment TABLE 8B-continued comparative storage stability of different
anti c-Met Nanobody constructs

| Construct | Storage stability (7.5 weeks incubation) | |
|---|---|---|
| | 25° C. | 40° C. |

(*) = sample was opalescent.

Example 6

Affinity Determination Using Surface Plasmon Resonance

Kinetic analysis of the anti-c-Met Nanobody-Alb fusion constructs A007900171 (SEQ ID NO:40) and A007901219 (SEQ ID NO:23) for human, cynomolgus and mouse serum albumin was performed using Surface Plasmon Resonance on the Biacore T100 instrument. HBS-EP+ buffer (0.01M HEPES buffer containing 0.15M NaCl, 3 mM EDTA and 0.05% Surfactant p20, pH7.4) was used as the running buffer and experiments were performed at 25° C. Serum albumin was chemically coupled on a Series S sensorchip chip CM5 with carboxymethylated dextran surface by a manual immo- Example 7

Binding of the MET-Ligand HGF in Alphascreen Assay

The anti-c-MET/anti-serum albumin Nanobody constructs were characterized in an HGF/c-MET competition AlphaScreen assay to evaluate their blocking potency and efficacy and compare this with a benchmark antibody fragment (5D5 Fab v2). A dilution series of anti-c-MET Nanobodies and benchmark 5D5 Fab v2 starting from 250 nM up to 0.9 pM was pre-incubated with 100 pM biotinylated hHGF during 15 minutes at RT. To this mixture the anti-human Fc conjugated acceptor beads and c-MET/Fc (100 μM final concentration) were added and incubated for 2 hours at RT. Next, streptavidin donor beads were added and the mixture was incubated for 1 additional hour. Fluorescence was measured by reading plates on the EnVision Multilabel Plate Reader using an excitation wavelength of 680 nm and an emission wavelength of 520 nm.

The two constructs effectively inhibit the HGF binding to c-MET receptor in a dose-dependent manner. The calculated $IC_{50}$ values and corresponding 95% confidence intervals are shown in Table 10. A007900171 and the two batches of A007901219 have similar IC50 values; their 95% CI are overlapping, which suggests that the difference is statistically not significant. The Nanobodies showed an >5-fold improved potency as compared to the benchmark 5D5 Fab v2.

TABLE 10

Inhibition of HGF binding to cMET as determined by Alphascreen (IC50 values and 95% confidence intervals)

| ID | IC$_{50}$ [in pM] | 95% CI [in pM] |
|---|---|---|
| 5D5 Fab v2 | 380 | 330 to 440 |
| A007900171 (Alb11) | 58 | 50 to 66 |
| A007901219 (Alb23) | 66 | 57 to 78 |

Example 8

Blocking the HGF-Induced MET Phosphorylation in the A549 Cancer Cell Line

The purified anti-c-MET/anti-serum albumin Nanobody constructs were characterized in the HGF-dependent phosphorylation assay. A dilution series of the anti-cMET constructs or the anti-cMET benchmark 5D5 Fab v2 starting from 1 µM up to 0.23 nM was co-incubated with 1 nM HGF on A549 cells during 15 min at 37° C. ⅓ of the lysed cell solution was then applied to the phospho c-MET MSD assay plates. Two duplicates on cell culture level were pooled on MSD level. After washing away unbound material, a sulfo tagged detection cMET antibody detected both the phosphorylated as well as the unphosphorylated receptor. The read out was performed with the sector imager 2400.

The two anti-c-MET/anti-serum albumin Nanobody constructs effectively inhibit the HGF-dependent c-MET receptor phosphorylation in a dose-dependent manner. The calculated IC$_{50}$ values and corresponding 95% confidence intervals are shown in 11. A007900171 and the two batches of A007901219 have similar IC$_{50}$ values; their 95% CI are overlapping, which suggests that the differences are statistically not significant. The Nanobodies showed a ca. 2-fold improved potency as compared to the benchmark 5D5 Fab v2. Additionally, within 95% confidence intervals, the addition of human serum albumin to the stimulated cells did not alter IC$_{50}$ values of the tested Nanobodies.

TABLE 11

Inhibition of HGF binding to cMET as determined by cMET phosphorylation assay (IC50 values and 95% confidence intervals)

| | −HSA | | +HSA | |
|---|---|---|---|---|
| ID | IC$_{50}$ [in nM] | 95% CI [in nM] | IC$_{50}$ [in nM] | 95% CI [in nM] |
| 5D5 Fab v2 | 11.9 | 8.57 to 16.5 | n.d. | |
| A007900171 (Alb11) | 5.97 | 5.08 to 7.00 | 6.28 | 5.35 to 7.36 |
| A007901219 (Alb23) | 5.41 | 4.61 to 6.35 | 4.20 | 3.60 to 4.91 |

The entire contents of all of the references (including literature references, issued patents, published patent applications, and co pending patent applications) cited throughout this application are hereby expressly incorporated by reference, in particular for the teaching that is referenced herein.

The invention claimed is:

1. An albumin binding polypeptide, protein, construct, compound or other chemical entity that comprises or essentially consists of the amino acid sequence Alb-23 (SEQ ID NO:1) or a variant of Alb-23 and one or more other amino acid sequences, binding domains, binding units or other moieties or chemical entities, suitably linked to each other either directly via suitable linkers or spacers, in which said variant of Alb-23 comprises:
   (i) the amino acid motif GP on positions 44 and 45;
   (ii) the amino acid motif SKN on positions 74 to 76;
   (iii) a CDR1 that is the amino acid sequence SFGMS (SEQ ID NO:29);
   (iv) a CDR2 that is the amino acid sequence SISGSGS-DTLYADSVKG (SEQ ID NO:30);
   (v) a CDR3 that is the amino acid sequence GGSLSR (SEQ ID NO:31), and that further comprises between 1 and 7 further amino acid differences with the sequence given in SEQ ID NO:1.

2. The albumin binding polypeptide, protein, construct, compound or other chemical entity according to claim 1, in which said variant of Alb-23 also comprises
   (vi) a G at position 16; and/or
   (vii) an R at position 83.

3. The albumin binding polypeptide, protein, construct, compound or other chemical entity according to claim 1, that comprises or essentially consists of the amino acid sequence Alb-23 (SEQ ID NO:1) and one or more other amino acid sequences, binding domains, binding units or other moieties or chemical entities, suitably linked to each other either directly suitable linkers or spacers.

4. The albumin binding polypeptide, protein, construct, compound or other chemical entity according to claim 1, in which said one or more other amino acid sequences, binding domains, binding units or other moieties or chemical entities are one or more therapeutic amino acid sequences, binding domains, binding units, moieties or entities.

5. The albumin binding polypeptide, protein or construct according to claim 1, in which the one or more other amino acid sequences, binding domains, binding units or other moieties or chemical entities are one or more immunoglobulin single variable domains or Nanobodies.

6. The albumin binding polypeptide, protein or construct according to claim 5, in which at least one of the immunoglobulin single variable domains or Nanobodies comprises at least two disulphide bridges.

7. The albumin binding polypeptide, protein or construct according to claim 6, in which at least one of the Nanobodies is a Nanobody of VHH Class I.

8. The albumin binding polypeptide, protein or construct according to claim 5, in which at least one of the immunoglobulin single variable domains or Nanobodies are directed against c-met.

9. The albumin binding polypeptide, protein or construct according to claim 8, in which at least one of the immunoglobulin single variable domain or Nanobody directed against c-met comprises two disulphide bridges.

10. The albumin binding polypeptide, protein or construct according to claim 8, in which said immunoglobulin single variable domain or Nanobody against c-met is 4E09 (SEQ ID NO:12) or a humanized variant of 4E09.

11. The albumin binding polypeptide, protein or construct according to claim 8, in which said immunoglobulin single variable domain or Nanobody against c-met is A00790105 (SEQ ID NO:19).

12. The albumin binding polypeptide, protein or construct according to claim 11, which is A00790105-9GS-Alb23 (SEQ ID NO:23) or a variant of SEQ ID NO:23 in which said variant of SEQ ID NO:23 comprises the following amino acid motifs or differences in the Alb-23 portion (SEQ ID NO:1) of SEQ ID NO:23:
 (i) the amino acid motif GP on positions 44 and 45;
 (ii) the amino acid motif SKN on positions 74 to 76;
 (iii) a CDR1 that is the amino acid sequence SFGMS (SEQ ID NO:29);
 (iv) a CDR2 that is the amino acid sequence SISGSGS-DTLYADSVKG (SEQ ID NO:30);
 (v) a CDR3 that is the amino acid sequence GGSLSR (SEQ ID NO:31),
and that further comprises between 1 and 7 further amino acid differences with the sequence given in SEQ ID NO:1.

13. The albumin binding polypeptide, protein, construct, compound or other chemical entity according to claim 3, in which said one or more other amino acid sequences, binding domains, binding units or other moieties or chemical entities are one or more therapeutic amino acid sequences, binding domains, binding units, moieties or chemical entities.

14. The albumin binding polypeptide, protein or construct according to claim 13, in which the one or more other amino acid sequences, binding domains, binding units or other moieties or chemical entities are one or more immunoglobulin single variable domains or Nanobodies.

15. The albumin binding polypeptide, protein or construct according to claim 14, in which at least one of the immunoglobulin single variable domains or Nanobodies comprises at least two disulphide bridges.

16. The albumin binding polypeptide, protein or construct according to claim 15, in which at least one of the Nanobodies is a Nanobody of VHH Class I.

17. The albumin binding polypeptide, protein or construct according to claim 14, in which at least one of the immunoglobulin single variable domains or Nanobodies are directed against c-met.

18. The albumin binding polypeptide, protein or construct according to claim 17, in which said immunoglobulin single variable domain or Nanobody against c-met is 4E09 (SEQ ID NO:12) or a humanized variant of 4E09.

19. The albumin binding polypeptide, protein or construct according to claim 17, in which said immunoglobulin single variable domain or Nanobody against c-met is A00790105 (SEQ ID NO:19).

20. The albumin binding polypeptide, protein or construct according to claim 19, which is A00790105-9GS-Alb23 (SEQ ID NO:23) or a variant of SEQ ID NO:23 in which said variant of SEQ ID NO:23 comprises the following amino acid motifs or differences in the Alb-23 portion (SEQ ID NO: 1) of SEQ ID NO:23:
 (i) the amino acid motif GP on positions 44 and 45;
 (ii) the amino acid motif SKN on positions 74 to 76;
 (iii) a CDR1 that is the amino acid sequence SFGMS (SEQ ID NO:29);
 (iv) a CDR2 that is the amino acid sequence SISGSGS-DTLYADSVKG (SEQ ID NO:30);
 (v) a CDR3 that is the amino acid sequence GGSLSR (SEQ ID NO:31),
and that further comprises between 1 and 7 further amino acid differences with the sequence given in SEQ ID NO:1.

* * * * *

SEQUENCE LISTING

<160> NUMBER OF SEQ ID NOS: 49

<210> SEQ ID NO 1
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 2
<211> LENGTH: 115

```
<212> TYPE: PRT
<213> ORGANISM: Artificial Sequence
<220> FEATURE:
<223> OTHER INFORMATION: nanobody or nanobody construct

<400> SEQUENCE: 2

Ala Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 3
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 3

Ala Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 4

Ala Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
```

```
                    20                  25                  30
Gly Met Ser Trp Val Arg Gln Ala Pro Gly Lys Gly Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 6
<211> LENGTH: 116
<212> TYPE: PRT
<213> ORGANISM: Artificial Sequence
<220> FEATURE:
<223> OTHER INFORMATION: nanobody or nanobody construct

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala
        115

<210> SEQ ID NO 7
<211> LENGTH: 117
<212> TYPE: PRT
<213> ORGANISM: Artificial Sequence
<220> FEATURE:
<223> OTHER INFORMATION: nanobody or nanobody construct

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala
        115

<210> SEQ ID NO 8
<211> LENGTH: 118
<212> TYPE: PRT
<213> ORGANISM: Artificial Sequence
<220> FEATURE:
<223> OTHER INFORMATION: nanobody or nanobody construct

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Ala Ala Ala
        115

<210> SEQ ID NO 9
```

-continued

```
<211> LENGTH: 116
<212> TYPE: PRT
<213> ORGANISM: Artificial Sequence
<220> FEATURE:
<223> OTHER INFORMATION: nanobody or nanobody construct

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly
        115

<210> SEQ ID NO 10
<211> LENGTH: 117
<212> TYPE: PRT
<213> ORGANISM: Artificial Sequence
<220> FEATURE:
<223> OTHER INFORMATION: nanobody or nanobody construct

<400> SEQUENCE: 10

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly
        115

<210> SEQ ID NO 11
<211> LENGTH: 118
<212> TYPE: PRT
<213> ORGANISM: Artificial Sequence
<220> FEATURE:
<223> OTHER INFORMATION: nanobody or nanobody construct

<400> SEQUENCE: 11

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Arg Ser Phe
             20                  25                  30

Gly Met Ser Trp Val Arg Gln Ala Pro Gly Lys Gly Pro Glu Trp Val
         35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser Gly Gly Gly
        115

<210> SEQ ID NO 12
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
             20                  25                  30

Ala Ile Gly Trp Phe Arg Gln Ala Pro Gly Lys Glu Arg Glu Gly Val
         35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                 85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 13
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
             20                  25                  30

Ala Ile Gly Trp Phe Arg Gln Ala Pro Gly Lys Glu Arg Glu Gly Val
         35                  40                  45

Ser Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

```
Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 14
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Ser Ile Asp Ala Ser Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Gly Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 15
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 15

Glu Val Gln Leu Val Glu Ser Gly Gly Gly Leu Val Gln Pro Gly Gly
1               5                   10                  15

Ser Leu Arg Leu Ser Ala Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Ser
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser
        115                 120                 125
```

-continued

```
<210> SEQ ID NO 16
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Ser Cys Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 17
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Gly Val Tyr Tyr Cys
                85                  90                  95

Ala Thr Pro Ile Gly Leu Ser Ser Ser Cys Leu Leu Glu Tyr Asp Tyr
            100                 105                 110

Asp Tyr Trp Gly Gln Gly Thr Leu Val Thr Val Ser Ser
        115                 120                 125

<210> SEQ ID NO 18
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 18

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
                35                  40                  45

Leu Cys Ile Asp Ala Ser Asp Asp Ile Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
                100                 105                 110

Asp Tyr Trp Gly Gln Gly Thr Leu Val Thr Val Ser Ser
            115                 120                 125

<210> SEQ ID NO 19
<211> LENGTH: 125
<212> TYPE: PRT
<213> ORGANISM: Artificial Sequence
<220> FEATURE:
<223> OTHER INFORMATION: nanobody or nanobody construct

<400> SEQUENCE: 19

Asp Val Gln Leu Val Glu Ser Gly Gly Gly Leu Val Gln Pro Gly Gly
 1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
                35                  40                  45

Leu Cys Ile Asp Ala Ser Asp Asp Ile Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
                100                 105                 110

Asp Tyr Trp Gly Gln Gly Thr Leu Val Thr Val Ser Ser
            115                 120                 125

<210> SEQ ID NO 20
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 20

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Pro Glu Asp Thr Ala Val Tyr Tyr Cys
                    85                  90                  95

Thr Ile Gly Gly Ser Leu Ser Arg Ser Ser Gln Gly Thr Leu Val Thr
                100                 105                 110

Val Ser Ser Gly Gly Gly Gly Ser Gly Gly Gly Ser Glu Val Gln Leu
                115                 120                 125

Val Glu Ser Gly Gly Gly Leu Val Gln Pro Gly Gly Ser Leu Arg Leu
            130                 135                 140

Ser Cys Ala Ala Ser Gly Phe Ile Leu Asp Tyr Tyr Ala Ile Gly Trp
145                 150                 155                 160

Phe Arg Gln Ala Pro Gly Lys Glu Arg Glu Gly Val Leu Cys Ile Asp
                165                 170                 175

Ala Ser Asp Asp Ile Thr Tyr Tyr Ala Asp Ser Val Lys Gly Arg Phe
                180                 185                 190

Thr Ile Ser Arg Asp Asn Ala Lys Asn Thr Val Tyr Leu Gln Met Asn
                195                 200                 205

Ser Leu Lys Pro Glu Asp Thr Gly Val Tyr Tyr Cys Ala Thr Pro Ile
            210                 215                 220

Gly Leu Ser Ser Cys Leu Leu Glu Tyr Asp Tyr Asp Tyr Trp Gly
225                 230                 235                 240

Gln Gly Thr Leu Val Thr Val Ser Ser
                245
```

<210> SEQ ID NO 21
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
                20                  25                  30

Ala Ile Gly Trp Phe Arg Gln Ala Pro Gly Lys Glu Arg Glu Gly Val
            35                  40                  45

Leu Cys Ile Asp Ala Ser Asp Asp Ile Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Glu Tyr Asp Tyr
                100                 105                 110

Asp Tyr Trp Gly Gln Gly Thr Leu Val Thr Val Ser Ser Gly Gly Gly
            115                 120                 125

Gly Ser Gly Gly Gly Ser Glu Val Gln Leu Leu Glu Ser Gly Gly Gly
        130                 135                 140

Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Gly Pro Glu Trp Val Ser Ser Ile Ser Gly Ser Gly Ser Asp Thr
```

```
                180             185                 190
Leu Tyr Ala Asp Ser Val Lys Gly Arg Phe Thr Ile Ser Arg Asp Asn
            195                 200             205

Ser Lys Asn Thr Leu Tyr Leu Gln Met Asn Ser Leu Arg Pro Glu Asp
        210             215                 220

Thr Ala Val Tyr Tyr Cys Thr Ile Gly Gly Ser Leu Ser Arg Ser Ser
225             230                 235                 240

Gln Gly Thr Leu Val Thr Val Ser Ser
            245

<210> SEQ ID NO 22
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser Gly Gly Gly Gly Ser Gly Gly Gly Ser Asp Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Ile Leu Asp Tyr Tyr Ala Ile Gly Trp
145                 150                 155                 160

Phe Arg Gln Ala Pro Gly Lys Glu Arg Glu Gly Val Leu Cys Ile Asp
                165                 170                 175

Ala Ser Asp Asp Ile Thr Tyr Tyr Ala Asp Ser Val Lys Gly Arg Phe
            180                 185                 190

Thr Ile Ser Arg Asp Asn Ser Lys Asn Thr Val Tyr Leu Gln Met Asn
        195                 200                 205

Ser Leu Arg Pro Glu Asp Thr Ala Val Tyr Tyr Cys Ala Thr Pro Ile
    210                 215                 220

Gly Leu Ser Ser Ser Cys Leu Leu Glu Tyr Asp Tyr Asp Tyr Trp Gly
225                 230                 235                 240

Gln Gly Thr Leu Val Thr Val Ser Ser
            245

<210> SEQ ID NO 23
<211> LENGTH: 249
<212> TYPE: PRT
<213> ORGANISM: Artificial Sequence
<220> FEATURE:
<223> OTHER INFORMATION: nanobody or nanobody construct
```

```
<400> SEQUENCE: 23

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Leu Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Gly Pro Glu Trp Val Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
                245

<210> SEQ ID NO 24
<211> LENGTH: 275
<212> TYPE: PRT
<213> ORGANISM: Artificial Sequence
<220> FEATURE:
<223> OTHER INFORMATION: nanobody or nanobody construct

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95
```

```
Thr Ile Gly Gly Ser Leu Ser Arg Ser Ser Gln Gly Thr Leu Val Thr
                100                 105                 110

Val Ser Ser Gly Gly Gly Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Glu Val Gln Leu Val Glu Ser Gly Gly
145                 150                 155                 160

Leu Val Gln Pro Gly Gly Ser Leu Arg Leu Ser Cys Ala Ala Ser Gly
                165                 170                 175

Phe Ile Leu Asp Tyr Tyr Ala Ile Gly Trp Phe Arg Gln Ala Pro Gly
                180                 185                 190

Lys Glu Arg Glu Gly Val Leu Cys Ile Asp Ala Ser Asp Ile Thr
                195                 200                 205

Tyr Tyr Ala Asp Ser Val Lys Gly Arg Phe Thr Ile Ser Arg Asp Asn
                210                 215                 220

Ala Lys Asn Thr Val Tyr Leu Gln Met Asn Ser Leu Lys Pro Glu Asp
225                 230                 235                 240

Thr Gly Val Tyr Tyr Cys Ala Thr Pro Ile Gly Leu Ser Ser Ser Cys
                245                 250                 255

Leu Leu Glu Tyr Asp Tyr Asp Tyr Trp Gly Gln Gly Thr Leu Val Thr
                260                 265                 270

Val Ser Ser
        275

<210> SEQ ID NO 25
<211> LENGTH: 275
<212> TYPE: PRT
<213> ORGANISM: Artificial Sequence
<220> FEATURE:
<223> OTHER INFORMATION: nanobody or nanobody construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Ser Cys Leu Leu Glu Tyr Asp Tyr
                100                 105                 110

Asp Tyr Trp Gly Gln Gly Thr Leu Val Thr Val Ser Ser Gly Gly Gly
            115                 120                 125

Gly Ser Gly Gly Gly Ser Gly Gly Gly Ser Gly Gly Gly
    130                 135                 140

Ser Gly Gly Gly Ser Gly Gly Gly Ser Gly Gly Gly Ser
145                 150                 155                 160

Glu Val Gln Leu Leu Glu Ser Gly Gly Gly Leu Val Gln Pro Gly Gly
                165                 170                 175
```

```
Ser Leu Arg Leu Ser Cys Ala Ala Ser Gly Phe Thr Phe Arg Ser Phe
            180                 185                 190
Gly Met Ser Trp Val Arg Gln Ala Pro Gly Lys Gly Pro Glu Trp Val
        195                 200                 205
Ser Ser Ile Ser Gly Ser Gly Ser Asp Thr Leu Tyr Ala Asp Ser Val
    210                 215                 220
Lys Gly Arg Phe Thr Ile Ser Arg Asp Asn Ser Lys Asn Thr Leu Tyr
225                 230                 235                 240
Leu Gln Met Asn Ser Leu Arg Pro Glu Asp Thr Ala Val Tyr Tyr Cys
                245                 250                 255
Thr Ile Gly Gly Ser Leu Ser Arg Ser Ser Gln Gly Thr Leu Val Thr
            260                 265                 270
Val Ser Ser
        275

<210> SEQ ID NO 26
<211> LENGTH: 275
<212> TYPE: PRT
<213> ORGANISM: Artificial Sequence
<220> FEATURE:
<223> OTHER INFORMATION: nanobody or nanobody construct

<400> SEQUENCE: 26

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Arg Ser Phe
            20                  25                  30
Gly Met Ser Trp Val Arg Gln Ala Pro Gly Lys Gly Pro Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser Gly Gly Gly Gly Ser Gly Gly Gly Ser Gly Gly Gly
        115                 120                 125
Gly Ser Gly Gly Gly Ser Gly Gly Gly Ser Gly Gly Gly
    130                 135                 140
Ser Gly Gly Gly Ser Asp Val Gln Leu Val Glu Ser Gly Gly Gly
145                 150                 155                 160
Leu Val Gln Pro Gly Gly Ser Leu Arg Leu Ser Cys Ala Ala Ser Gly
                165                 170                 175
Phe Ile Leu Asp Tyr Tyr Ala Ile Gly Trp Phe Arg Gln Ala Pro Gly
            180                 185                 190
Lys Glu Arg Glu Gly Val Leu Cys Ile Asp Ala Ser Asp Ile Thr
        195                 200                 205
Tyr Tyr Ala Asp Ser Val Lys Gly Arg Phe Thr Ile Ser Arg Asp Asn
    210                 215                 220
Ser Lys Asn Thr Val Tyr Leu Gln Met Asn Ser Leu Arg Pro Glu Asp
225                 230                 235                 240
Thr Ala Val Tyr Tyr Cys Ala Thr Pro Ile Gly Leu Ser Ser Cys
                245                 250                 255
```

Leu Leu Glu Tyr Asp Tyr Asp Tyr Trp Gly Gln Gly Thr Leu Val Thr
            260                 265                 270

Val Ser Ser
        275

<210> SEQ ID NO 27
<211> LENGTH: 275
<212> TYPE: PRT
<213> ORGANISM: Artificial Sequence
<220> FEATURE:
<223> OTHER INFORMATION: nanobody or nanobody construct

<400> SEQUENCE: 27

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Gly Gly Gly
        115                 120                 125

Gly Ser Gly Gly Gly Gly Ser Gly Gly Gly Ser Gly Gly Gly Gly
    130                 135                 140

Ser Gly Gly Gly Gly Ser Gly Gly Gly Ser Gly Gly Gly Gly Ser
145                 150                 155                 160

Glu Val Gln Leu Leu Glu Ser Gly Gly Gly Leu Val Gln Pro Gly Gly
                165                 170                 175

Ser Leu Arg Leu Ser Cys Ala Ala Ser Gly Phe Thr Phe Arg Ser Phe
            180                 185                 190

Gly Met Ser Trp Val Arg Gln Ala Pro Gly Lys Gly Pro Glu Trp Val
        195                 200                 205

Ser Ser Ile Ser Gly Ser Gly Ser Asp Thr Leu Tyr Ala Asp Ser Val
210                 215                 220

Lys Gly Arg Phe Thr Ile Ser Arg Asp Asn Ser Lys Asn Thr Leu Tyr
225                 230                 235                 240

Leu Gln Met Asn Ser Leu Arg Pro Glu Asp Thr Ala Val Tyr Tyr Cys
                245                 250                 255

Thr Ile Gly Gly Ser Leu Ser Arg Ser Ser Gln Gly Thr Leu Val Thr
            260                 265                 270

Val Ser Ser
        275

<210> SEQ ID NO 28
<211> LENGTH: 383
<212> TYPE: PRT
<213> ORGANISM: Artificial Sequence
<220> FEATURE:
<223> OTHER INFORMATION: nanobody or nanobody construct

<400> SEQUENCE: 28

```
Asp Val Gln Leu Val Glu Ser Gly Gly Gly Leu Val Gln Pro Gly Gly
  1               5                  10                 15

Ser Leu Arg Leu Ser Cys Ala Ala Ser Gly Phe Ile Leu Asp Tyr Tyr
             20                  25                  30

Ala Ile Gly Trp Phe Arg Gln Ala Pro Gly Lys Glu Arg Glu Gly Val
         35                  40                  45

Leu Cys Ile Asp Ala Ser Asp Asp Ile Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Pro Glu Asp Thr Ala Val Tyr Tyr Cys
             85                  90                  95

Ala Thr Pro Ile Gly Leu Ser Ser Cys Leu Leu Glu Tyr Asp Tyr
         100                 105                 110

Asp Tyr Trp Gly Gln Gly Thr Leu Val Thr Val Ser Ser Gly Gly Gly
         115                 120                 125

Gly Ser Gly Gly Gly Ser Asp Val Gln Leu Val Glu Ser Gly Gly Gly
     130                 135                 140

Leu Val Gln Pro Gly Gly Ser Leu Arg Leu Ser Cys Ala Ala Ser Gly
145                 150                 155                 160

Phe Ile Leu Asp Tyr Tyr Ala Ile Gly Trp Phe Arg Gln Ala Pro Gly
             165                 170                 175

Lys Glu Arg Glu Gly Val Leu Cys Ile Asp Ala Ser Asp Asp Ile Thr
             180                 185                 190

Tyr Tyr Ala Asp Ser Val Lys Gly Arg Phe Thr Ile Ser Arg Asp Asn
         195                 200                 205

Ser Lys Asn Thr Val Tyr Leu Gln Met Asn Ser Leu Arg Pro Glu Asp
     210                 215                 220

Thr Ala Val Tyr Tyr Cys Ala Thr Pro Ile Gly Leu Ser Ser Ser Cys
225                 230                 235                 240

Leu Leu Glu Tyr Asp Tyr Asp Tyr Trp Gly Gln Gly Thr Leu Val Thr
             245                 250                 255

Val Ser Ser Gly Gly Gly Gly Ser Gly Gly Gly Ser Glu Val Gln Leu
             260                 265                 270

Leu Glu Ser Gly Gly Gly Leu Val Gln Pro Gly Gly Ser Leu Arg Leu
         275                 280                 285

Ser Cys Ala Ala Ser Gly Phe Thr Phe Arg Ser Phe Gly Met Ser Trp
     290                 295                 300

Val Arg Gln Ala Pro Gly Lys Gly Pro Glu Trp Val Ser Ser Ile Ser
305                 310                 315                 320

Gly Ser Gly Ser Asp Thr Leu Tyr Ala Asp Ser Val Lys Gly Arg Phe
             325                 330                 335

Thr Ile Ser Arg Asp Asn Ser Lys Asn Thr Leu Tyr Leu Gln Met Asn
             340                 345                 350

Ser Leu Arg Pro Glu Asp Thr Ala Val Tyr Tyr Cys Thr Ile Gly Gly
         355                 360                 365

Ser Leu Ser Arg Ser Ser Gln Gly Thr Leu Val Thr Val Ser Ser
     370                 375                 380

<210> SEQ ID NO 29
<211> LENGTH: 5
<212> TYPE: PRT
<213> ORGANISM: Artificial Sequence
<220> FEATURE:
```

```
<223> OTHER INFORMATION: nanobody or nanobody construct

<400> SEQUENCE: 29

Ser Phe Gly Met Ser
1               5

<210> SEQ ID NO 30
<211> LENGTH: 17
<212> TYPE: PRT
<213> ORGANISM: Artificial Sequence
<220> FEATURE:
<223> OTHER INFORMATION: nanobody or nanobody construct

<400> SEQUENCE: 30

Ser Ile Ser Gly Ser Gly Ser Asp Thr Leu Tyr Ala Asp Ser Val Lys
1               5                   10                  15

Gly

<210> SEQ ID NO 31
<211> LENGTH: 6
<212> TYPE: PRT
<213> ORGANISM: Artificial Sequence
<220> FEATURE:
<223> OTHER INFORMATION: nanobody or nanobody construct

<400> SEQUENCE: 31

Gly Gly Ser Leu Ser Arg
1               5

<210> SEQ ID NO 32
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 33
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 33
```

```
Glu Val Gln Leu Val Glu Ser Gly Gly Gly Leu Val Gln Pro Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 34

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 35
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 35

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60
```

```
Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 36

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
        115

<210> SEQ ID NO 37
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 37

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
             20                  25                  30

Gly Met Ser Trp Val Arg Gln Ala Pro Gly Lys Gly Leu Glu Trp Val
         35                  40                  45

Ser Ser Ile Ser Gly Ser Gly Ser Asp Thr Leu Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
            100                 105                 110

Val Ser Ser
```

-continued

115

<210> SEQ ID NO 38
<211> LENGTH: 115
<212> TYPE: PRT
<213> ORGANISM: Artificial Sequence
<220> FEATURE:
<223> OTHER INFORMATION: nanobody or nanobody construct

<400> SEQUENCE: 38

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Gly Gln Gly Thr Leu Val Thr
            100                 105                 110

Val Ser Ser
        115

<210> SEQ ID NO 39
<211> LENGTH: 283
<212> TYPE: PRT
<213> ORGANISM: Artificial Sequence
<220> FEATURE:
<223> OTHER INFORMATION: nanobody or nanobody construct

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

```
Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
        210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Ala Ala Asp Tyr Lys Asp
            245                 250                 255

His Asp Gly Asp Tyr Lys Asp His Asp Ile Asp Tyr Lys Asp Asp Asp
            260                 265                 270

Asp Lys Gly Ala Ala His His His His His His
            275                 280

<210> SEQ ID NO 40
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 40

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
            85                  90                  95

Ala Thr Pro Ile Gly Leu Ser Ser Cys Leu Leu Glu Tyr Asp Tyr
        100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
        130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
            165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
        210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser
            245
```

```
<210> SEQ ID NO 41
<211> LENGTH: 246
<212> TYPE: PRT
<213> ORGANISM: Artificial Sequence
<220> FEATURE:
<223> OTHER INFORMATION: nanobody or nanobody construct

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Asp Met Ala Trp Val Arg Gln Ala Pro Gly Lys Arg Pro Glu Trp Val
        35                  40                  45

Ser Ser Ile Asp Thr Gly Gly Asp Ile Thr His Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Trp Cys
                85                  90                  95

Ala Thr Asp Glu Glu Tyr Ala Leu Gly Pro Asn Glu Phe Asp Tyr Tyr
            100                 105                 110

Gly Gln Gly Thr Leu Val Thr Val Ser Ser Gly Gly Gly Gly Ser Gly
        115                 120                 125

Gly Gly Ser Glu Val Gln Leu Leu Glu Ser Gly Gly Gly Leu Val Gln
    130                 135                 140

Pro Gly Gly Ser Leu Arg Leu Ser Cys Ala Ala Ser Gly Phe Thr Phe
145                 150                 155                 160

Arg Ser Phe Gly Met Ser Trp Val Arg Gln Ala Pro Gly Lys Gly Pro
                165                 170                 175

Glu Trp Val Ser Ser Ile Ser Gly Ser Gly Ser Asp Thr Leu Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Pro Glu Asp Thr Ala Val
    210                 215                 220

Tyr Tyr Cys Thr Ile Gly Gly Ser Leu Ser Arg Ser Ser Gln Gly Thr
225                 230                 235                 240

Leu Val Thr Val Ser Ser
                245

<210> SEQ ID NO 42
<211> LENGTH: 246
<212> TYPE: PRT
<213> ORGANISM: Artificial Sequence
<220> FEATURE:
<223> OTHER INFORMATION: nanobody or nanobody construct

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Tyr
            20                  25                  30

Asp Met Ala Trp Val Arg Gln Ala Pro Gly Lys Arg Pro Glu Trp Val
        35                  40                  45

Ser Ser Ile Asp Thr Gly Gly Asp Ile Thr His Tyr Ala Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Trp Cys
             85                  90                  95

Ala Thr Asp Glu Glu Tyr Ala Leu Gly Pro Asn Glu Phe Asp Tyr Tyr
            100                 105                 110

Gly Gln Gly Thr Leu Val Thr Val Ser Ser Gly Gly Gly Gly Ser Gly
        115                 120                 125

Gly Gly Ser Glu Val Gln Leu Val Glu Ser Gly Gly Gly Leu Val Gln
130                 135                 140

Pro Gly Asn Ser Leu Arg Leu Ser Cys Ala Ala Ser Gly Phe Thr Phe
145                 150                 155                 160

Ser Ser Phe Gly Met Ser Trp Val Arg Gln Ala Pro Gly Lys Gly Leu
                165                 170                 175

Glu Trp Val Ser Ser Ile Ser Gly Ser Gly Ser Asp Thr Leu Tyr Ala
            180                 185                 190

Asp Ser Val Lys Gly Arg Phe Thr Ile Ser Arg Asp Asn Ala Lys Thr
        195                 200                 205

Thr Leu Tyr Leu Gln Met Asn Ser Leu Arg Pro Glu Asp Thr Ala Val
    210                 215                 220

Tyr Tyr Cys Thr Ile Gly Gly Ser Leu Ser Arg Ser Ser Gln Gly Thr
225                 230                 235                 240

Leu Val Thr Val Ser Ser
                245
```

```
<210> SEQ ID NO 43
<211> LENGTH: 122
<212> TYPE: PRT
<213> ORGANISM: Artificial Sequence
<220> FEATURE:
<223> OTHER INFORMATION: nanobody or nanobody construct

<400> SEQUENCE: 43
```

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Asn Tyr
             20                  25                  30

Asp Met Ala Trp Val Arg Gln Ala Pro Gly Lys Arg Pro Glu Trp Val
         35                  40                  45

Ser Ser Ile Asp Thr Gly Gly Asp Ile Thr His Tyr Ala Asp Ser Val
     50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Trp Cys
             85                  90                  95

Ala Thr Asp Glu Glu Tyr Ala Leu Gly Pro Asn Glu Phe Asp Tyr Tyr
            100                 105                 110

Gly Gln Gly Thr Leu Val Thr Val Ser Ser
        115                 120
```

```
<210> SEQ ID NO 44
<211> LENGTH: 433
<212> TYPE: PRT
<213> ORGANISM: Artificial Sequence
<220> FEATURE:
<223> OTHER INFORMATION: nanobody or nanobody construct
```

<400> SEQUENCE: 44

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Ser Gly Gly Gly Gly Ser Gly Gly Gly Gly Ser Glu
145                 150                 155                 160

Val Gln Leu Val Glu Ser Gly Gly Gly Leu Val Gln Pro Gly Gly Ser
                165                 170                 175

Leu Arg Leu Ser Cys Ala Ala Ser Gly Arg Thr Phe Ser Ser Ile Tyr
            180                 185                 190

Ala Lys Gly Trp Phe Arg Gln Ala Pro Gly Lys Glu Arg Glu Phe Val
        195                 200                 205

Ala Ala Ile Ser Arg Ser Gly Arg Ser Thr Ser Tyr Ala Asp Ser Val
    210                 215                 220

Lys Gly Arg Phe Thr Ile Ser Arg Asp Asn Ser Lys Asn Thr Val Tyr
225                 230                 235                 240

Leu Gln Met Asn Ser Leu Arg Pro Glu Asp Thr Ala Val Tyr Tyr Cys
                245                 250                 255

Ala Ala Val Gly Gly Ala Thr Thr Val Thr Ala Ser Glu Trp Asp Tyr
            260                 265                 270

Trp Gly Gln Gly Thr Leu Val Thr Val Ser Ser Gly Gly Gly Gly Ser
        275                 280                 285

Gly Gly Gly Gly Ser Gly Gly Gly Ser Gly Gly Gly Gly Ser Gly
    290                 295                 300

Gly Gly Ser Gly Gly Gly Ser Gly Gly Gly Gly Ser Glu Val
305                 310                 315                 320

Gln Leu Val Glu Ser Gly Gly Gly Leu Val Gln Pro Gly Asn Ser Leu
                325                 330                 335

Arg Leu Ser Cys Ala Ala Ser Gly Phe Thr Phe Ser Ser Phe Gly Met
            340                 345                 350

Ser Trp Val Arg Gln Ala Pro Gly Lys Gly Leu Glu Trp Val Ser Ser
        355                 360                 365

Ile Ser Gly Ser Gly Ser Asp Thr Leu Tyr Ala Asp Ser Val Lys Gly
    370                 375                 380

Arg Phe Thr Ile Ser Arg Asp Asn Ala Lys Thr Thr Leu Tyr Leu Gln
385                 390                 395                 400

Met Asn Ser Leu Arg Pro Glu Asp Thr Ala Val Tyr Tyr Cys Thr Ile
                405                 410                 415
```

Gly Gly Ser Leu Ser Arg Ser Ser Gln Gly Thr Leu Val Thr Val Ser
            420                 425                 430

Ser

<210> SEQ ID NO 45
<211> LENGTH: 250
<212> TYPE: PRT
<213> ORGANISM: Artificial Sequence
<220> FEATURE:
<223> OTHER INFORMATION: nanobody or nanobody construct

<400> SEQUENCE: 45

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45

Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Thr Pro Ile Gly Leu Ser Ser Cys Leu Leu Glu Tyr Asp Tyr
            100                 105                 110

Asp Tyr Trp Gly Gln Gly Thr Leu Val Thr Val Ser Ser Gly Gly Gly
        115                 120                 125

Gly Ser Gly Gly Gly Ser Glu Val Gln Leu Leu Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Arg Ser Phe Gly Met Ser Trp Val Arg Gln Ala Pro Gly
                165                 170                 175

Lys Gly Pro Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Ala
                245                 250

<210> SEQ ID NO 46
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 46

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Glu Glu Arg Glu Gly Val
            35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Gly Gly Gly Gly
            115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
            195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 47
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 47

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Leu Gly Val
            35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
                100                 105                 110

Tyr Trp Gly Gln Gly Thr Leu Val Thr Val Ser Ser Gly Gly Gly Gly
            115                 120                 125

Ser Gly Gly Gly Ser Glu Val Gln Leu Val Glu Ser Gly Gly Gly Leu
    130                 135                 140

```
Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245

<210> SEQ ID NO 48
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 48

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Ile Gly Trp Phe Arg Gln Ala Pro Gly Glu Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245
```

```
<210> SEQ ID NO 49
<211> LENGTH: 249
<212> TYPE: PRT
<213> ORGANISM: Artificial Sequence
<220> FEATURE:
<223> OTHER INFORMATION: nanobody or nanobody construct

<400> SEQUENCE: 49

Asp Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Asp Asp Tyr
            20                  25                  30

Ala Ile Gly Trp Phe Arg Gln Ala Pro Gly Glu Glu Arg Leu Gly Val
        35                  40                  45

Ser Ser Ile Ser Ser Thr Tyr Gly Leu Thr Tyr Tyr Ala Asp Ser Val
    50                  55                  60

Lys Gly Arg Phe Thr Ile Ser Ser Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Thr Pro Ile Gly Leu Ile Gly Leu Asp Ala Tyr Glu Tyr Asp
            100                 105                 110

Tyr Trp Gly Gln Gly Thr Leu Val Thr Val Ser Ser Gly Gly Gly Gly
        115                 120                 125

Ser Gly Gly Gly Ser Glu Val Gln Leu Val Glu Ser Gly Gly Gly Leu
    130                 135                 140

Val Gln Pro Gly Asn Ser Leu Arg Leu Ser Cys Ala Ala Ser Gly Phe
145                 150                 155                 160

Thr Phe Ser Ser Phe Gly Met Ser Trp Val Arg Gln Ala Pro Gly Lys
                165                 170                 175

Gly Leu Glu Trp Val Ser Ser Ile Ser Gly Ser Gly Ser Asp Thr Leu
            180                 185                 190

Tyr Ala Asp Ser Val Lys Gly Arg Phe Thr Ile Ser Arg Asp Asn Ala
        195                 200                 205

Lys Thr Thr Leu Tyr Leu Gln Met Asn Ser Leu Arg Pro Glu Asp Thr
    210                 215                 220

Ala Val Tyr Tyr Cys Thr Ile Gly Gly Ser Leu Ser Arg Ser Ser Gln
225                 230                 235                 240

Gly Thr Leu Val Thr Val Ser Ser Ala
                245
```